(12) United States Patent
Uchiyama et al.

(10) Patent No.: US 11,254,975 B2
(45) Date of Patent: Feb. 22, 2022

(54) METHOD OF AMPLIFYING A POLYNUCLEOTIDE OF INTEREST

(71) Applicant: NATIONAL CENTER FOR CHILD HEALTH AND DEVELOPMENT, Tokyo (JP)

(72) Inventors: Toru Uchiyama, Tokyo (JP); Masafumi Onodera, Tokyo (JP)

(*) Notice: Subject to any disclaimer, the term of this patent is extended or adjusted under 35 U.S.C. 154(b) by 186 days.

(21) Appl. No.: 16/421,295

(22) Filed: May 23, 2019

(65) Prior Publication Data

US 2019/0360031 A1 Nov. 28, 2019

Related U.S. Application Data

(60) Provisional application No. 62/675,888, filed on May 24, 2018.

(51) Int. Cl.
| | | |
|---|---|---|
| *C12Q 1/68* | (2018.01) | |
| *C12Q 1/6848* | (2018.01) | |
| *C12Q 1/682* | (2018.01) | |
| *C12Q 1/6851* | (2018.01) | |
| *C12Q 1/686* | (2018.01) | |
| *C12Q 1/6811* | (2018.01) | |
| *C12Q 1/6827* | (2018.01) | |

(52) U.S. Cl.
CPC .......... *C12Q 1/6848* (2013.01); *C12Q 1/682* (2013.01); *C12Q 1/686* (2013.01); *C12Q 1/6811* (2013.01); *C12Q 1/6827* (2013.01); *C12Q 1/6851* (2013.01); *C12Q 2600/106* (2013.01); *C12Q 2600/112* (2013.01); *C12Q 2600/156* (2013.01); *C12Q 2600/16* (2013.01)

(58) Field of Classification Search
CPC ................... C12Q 1/68; C12N 15/00
USPC ........................................................ 435/6.1
See application file for complete search history.

(56) References Cited

U.S. PATENT DOCUMENTS

| | | | | |
|---|---|---|---|---|
| 10,927,419 | B2* | 2/2021 | Fan | C12Q 1/6876 |
| 2015/0141261 | A1* | 5/2015 | Hunicke-Smith | C12Q 1/6806 506/2 |
| 2019/0345537 | A1* | 11/2019 | Gerard | C12Q 1/6806 |
| 2020/0216840 | A1* | 7/2020 | Tanno | C12N 15/1006 |
| 2020/0255891 | A1* | 8/2020 | Ellington | C12Q 1/686 |
| 2020/0385785 | A1* | 12/2020 | Chen | C12Q 1/6806 |

FOREIGN PATENT DOCUMENTS

WO   WO-2012048341 A1 *  4/2012  ......... C12N 15/1065

OTHER PUBLICATIONS

Kim et al., Single-cell RT-PCR in microfluidic droplets with integrated chemical lysis, Anal. Chem. 2018, 90, 2, 1273-1279, Publication Date:Dec. 19, 2017.*
Klein et al., Droplet barcoding for single-cell transcriptomics applied to embryonic stem cells, Cell. May 21, 2015;161(5):1187-1201. doi: 10.1016/j.cell.2015.04.044.*

(Continued)

*Primary Examiner* — Aaron A Priest

(57) ABSTRACT

A method of amplifying a target nucleic acid (polynucleotide) contained in a particle including an enclosing lipid bilayer membrane according to the present invention includes the steps of:
  lysing the particle which is stored in a compartment constituted by a liquid in an amount of 100 µl or less; and
  amplifying the target nucleic acid in the compartment.

18 Claims, 10 Drawing Sheets

Specification includes a Sequence Listing.

(56) References Cited

OTHER PUBLICATIONS

Villella, A.D., Yao, J., Getty, R.R., Juliar, B.E., Yiannoutsos, C., Hartwell, J.R., Cai, S., Sadat,M.A., Cornetta, K., Williams, D.A., and Pollok, K.E. (2005). Real-time PCR: an effective tool for measuring transduction efficiency in human hematopoietic progenitor cells. Mol. Ther. 11, 483-491.

Charrier, S., Ferrand, M., Zerbato, M., Precigout, G., Viornery, A., Bucher-Laurent, S., Benkhelifa-Ziyyat, S., Merten, O.W., Perea, J., and Galy, A. (2011). Quantification of lentiviral vector copy numbers in individual hematopoietic colony-forming cells shows vector dose-dependent effects on the frequency and level of transduction. Gene Ther. 18, 479-487.

Hindson, B.J., Ness, K.D., Masquelier, D.A., Belgrader, P., Heredia, N.J.,Makarewicz, A.J., Bright, I.J., Lucero, M.Y., Hiddessen, A.L., Legler, T.C., et al. (2011). Highthroughput droplet digital PCR system for absolute quantitation of DNA copy number. Anal. Chem. 83, 8604-8610.

Moser, D.A., Braga, L., Raso, A., Zacchigna, S., Giacca, M., and Simon, P. (2014). Transgene detection by digital droplet PCR. PLoS ONE 9, e111781.

Abyzov, A., Mariani, J., Palejev, D., Zhang, Y., Haney, M.S., Tomasini, L., Ferrandino, A.F., Rosenberg Belmaker, L. A., Szekely, A., Wilson, M., et al. (2012). Somatic copy number mosaicism in human skin revealed by induced pluripotent stem cells. Nature 492, 438-442.

Klein, A.M., Mazutis, L., Akartuna, I., Tallapragada, N., Veres, A., Li, V., Peshkin, L., Weitz, D.A., and Kirschner, M.W. (2015). Droplet barcoding for single-cell transcriptomics applied to embryonic stem cells. Cell 161, 1187-1201.

Yuka Igarashi et al., "Single Cell-Based Vector Tracing in Patients with ADA-SCID Treated with Stem Cell Gene Therapy" Molecular Therapy: Methods & Clinical Development vol. 6 Sep. 2017.

* cited by examiner

SEQUENCE LISTING

```
<160> NUMBER OF SEQ ID NOS: 6

<210> SEQ ID NO 1
<211> LENGTH: 22
<212> TYPE: DNA
```

```
<213> ORGANISM: Artificial Sequence
<220> FEATURE:
<223> OTHER INFORMATION: retrovirus forward primer

<400> SEQUENCE: 1
gcaacctatc tgtgtctgtc cg                                           22

<210> SEQ ID NO 2
<211> LENGTH: 19
<212> TYPE: DNA
<213> ORGANISM: Artificial Sequence
<220> FEATURE:
<223> OTHER INFORMATION: retrovirus reverse primer

<400> SEQUENCE: 2
ggtccgccag atacagagc                                               19

<210> SEQ ID NO 3
<211> LENGTH: 15
<212> TYPE: DNA
<213> ORGANISM: Artificial Sequence
<220> FEATURE:
<223> OTHER INFORMATION: retrovirus probe

<400> SEQUENCE: 3
gtctgtacta gttag                                                   15

<210> SEQ ID NO 4
<211> LENGTH: 20
<212> TYPE: DNA
<213> ORGANISM: Artificial Sequence
<220> FEATURE:
<223> OTHER INFORMATION: RPP30 forward probe

<400> SEQUENCE: 4
tccaggaggg agaattgatg                                              20

<210> SEQ ID NO 5
<211> LENGTH: 20
<212> TYPE: DNA
<213> ORGANISM: Artificial Sequence
<220> FEATURE:
<223> OTHER INFORMATION: RPP30 reverse probe

<400> SEQUENCE: 5
atggtccgtc tcaggaaatg                                              20

<210> SEQ ID NO 6
<211> LENGTH: 12
<212> TYPE: DNA
<213> ORGANISM: Artificial Sequence
<220> FEATURE:
<223> OTHER INFORMATION: RPP30 probe

<400> SEQUENCE: 6
tggcctgagc ag                                                      12
```

METHOD OF AMPLIFYING A POLYNUCLEOTIDE OF INTEREST

TECHNICAL FIELD

The present invention relates to method of amplifying a polynucleotide of interest.

BACKGROUND ART

Stem cell-based gene therapy has been proposed as a highly desirable treatment for primary immunodeficiencies (PIDs) when patients lack human leukocyte antigen (HLA)-matched suitable donors for hematopoietic stem cell transplantation (HSCT). The addition of the therapeutic gene to autologous hematopoietic stem cells (HSCs) is an attractive alternative because the gene-corrected HSCs are expected to reconstitute the functional immune system in the same manner as allogeneic HSCs in treated patients (Non-Patent Literatures 1-4). A series of HSCbased gene therapy clinical trials confirmed this expectation, revealing that treated patients displayed multi-lineage expression of the transduced gene (Non-Patent Literatures 5-12).

To achieve clinical improvement, sufficient engraftment of the transduced cells is required, although various factors, including the selective advantage of the therapeutic gene, affect their engraftment in bone marrow (BM) (Non-Patent Literatures 5, 6, 10-12). Therefore, the mapping of gene-transduced cell distributions in treated patients is required to evaluate the efficacy of gene therapy. Recently, advances in the genetic characterization of a single cell provided insights into genomic and transcriptomic heterogeneity (Non-Patent Literature 13), and such insights can be helpful in the field of gene therapy.

CITATION LIST

Non-Patent Literature

1. Bordignon, C., Notarangelo, L. D., Nobili, N., Ferrari, G., Casorati, G., Panina, P., Mazzolari, E., Maggioni, D., Rossi, C., Servida, P., et al. (1995). Gene therapy in peripheral blood lymphocytes and bone marrow for ADA-immunodeficient patients. Science 270, 470-475.
2. Kohn, D. B., Weinberg, K. I., Nolta, J. A., Heiss, L. N., Lenarsky, C., Crooks, G. M., Hanley, M. E., Annett, G., Brooks, J. S., el-Khoureiy, A., et al. (1995). Engraftment of gene-modified umbilical cord blood cells in neonates with adenosine deaminase deficiency. Nat. Med. 1, 1017-1023.
3. Malech, H. L., Maples, P. B., Whiting-Theobald, N., Linton, G. F., Sekhsaria, S., Vowells, S. J., Li, F., Miller, J. A., DeCarlo, E., Holland, S. M., et al. (1997). Prolonged production of NADPH oxidase-corrected granulocytes after gene therapy of chronic granulomatous disease. Proc. Natl. Acad. Sci. USA 94, 12133-12138.
4. Kohn, D. B., Hershfield, M. S., Carbonaro, D., Shigeoka, A., Brooks, J., Smogorzewska, E. M., Barsky, L. W., Chan, R., Burotto, F., Annett, G., et al. (1998). T lymphocytes with a normal ADA gene accumulate after transplantation of transduced autologous umbilical cord blood CD34+ cells in ADA-deficient SCID neonates. Nat. Med. 4, 775-780.
5. Cavazzana-Calvo, M., Hacein-Bey, S., de Saint Basile, G., Gross, F., Yvon, E., Nusbaum, P., Selz, F., Hue, C., Certain, S., Casanova, J. L., et al. (2000). Gene therapy of human severe combined immunodeficiency (SCID)-X1 disease. Science 288, 669-672.
6. Aiuti, A., Slavin, S., Aker, M., Ficara, F., Deola, S., Mortellaro, A., Morecki, S., Andolfi, G., Tabucchi, A., Carlucci, F., et al. (2002). Correction of ADA-SCID by stem cell gene therapy combined with nonmyeloablative conditioning. Science 296, 2410-2413.
7. Gaspar, H. B., Parsley, K. L., Howe, S., King, D., Gilmour, K. C., Sinclair, J., Brouns, G., Schmidt, M., Von Kalle, C., Barington, T., et al. (2004). Gene therapy of X-linked severe combined immunodeficiency by use of a pseudotyped gammaretroviral vector. Lancet 364, 2181-2187.
8. Gaspar, H. B., Bjorkegren, E., Parsley, K., Gilmour, K. C., King, D., Sinclair, J., Zhang, F., Giannakopoulos, A., Adams, S., Fairbanks, L. D., et al. (2006). Successful reconstitution of immunity in ADA-SCID by stem cell gene therapy following cessation of PEG-ADA and use of mild preconditioning. Mol. Ther. 14, 505-513.
9. Aiuti, A., Cattaneo, F., Galimberti, S., Benninghoff, U., Cassani, B., Callegaro, L., Scaramuzza, S., Andolfi, G., Mirolo, M., Brigida, I., et al. (2009). Gene therapy for immunodeficiency due to adenosine deaminase deficiency. N. Engl. J. Med. 360, 447-458.
10. Hacein-Bey-Abina, S., Hauer, J., Lim, A., Picard, C., Wang, G. P., Berry, C. C., Martinache, C., Rieux-Laucat, F., Latour, S., Belohradsky, B. H., et al. (2010). Efficacy of gene therapy for X-linked severe combined immunodeficiency. N. Engl. J. Med. 363, 355-364.
11. Gaspar, H. B., Cooray, S., Gilmour, K. C., Parsley, K. L., Adams, S., Howe, S. J., Al Ghonaium, A., Bayford, J., Brown, L., Davies, E. G., et al. (2011). Long-term persistence of a polyclonal T cell repertoire after gene therapy for X-linked severe combined immunodeficiency. Sci. Transl. Med. 3, 97ra79.
12. Gaspar, H. B., Cooray, S., Gilmour, K. C., Parsley, K. L., Zhang, F., Adams, S., Bjorkegren, E., Bayford, J., Brown, L., Davies, E. G., et al. (2011). Hematopoietic stem cell gene therapy for adenosine deaminase-deficient severe combined immunodeficiency leads to long-term immunological recovery and metabolic correction. Sci. Transl. Med. 3, 97ra80.
13. Macaulay, I. C., and Voet, T. (2014). Single cell genomics: advances and future perspectives. PLoS Genet. 10, e1004126.
14. Hershfield, M. S. (1998). Adenosine deaminase deficiency: clinical expression, molecular basis, and therapy. Semin. Hematol. 35, 291-298.
15. Hershfield, M. S., Buckley, R. H., Greenberg, M. L., Melton, A. L., Schiff, R., Hatem, C., Kurtzberg, J., Markert, M. L., Kobayashi, R. H., Kobayashi, A. L., et al. (1987). Treatment of adenosine deaminase deficiency with polyethylene glycol-modified adenosine deaminase. N. Engl. J. Med. 316, 589-596.
16. Chan, B., Wara, D., Bastian, J., Hershfield, M. S., Bohnsack, J., Azen, C. G., Parkman, R., Weinberg, K., and Kohn, D. B. (2005). Long-term efficacy of enzyme replacement therapy for adenosine deaminase (ADA)-deficient severe combined immunodeficiency (SCID). Clin. Immunol. 117, 133-143.
17. Candotti, F., Shaw, K. L., Muul, L., Carbonaro, D., Sokolic, R., Choi, C., Schurman, S. H., Garabedian, E., Kesserwan, C., Jagadeesh, G. J., et al. (2012). Gene therapy for adenosine deaminase-deficient severe combined immune deficiency: clinical comparison of retroviral vectors and treatment plans. Blood 120, 3635-3646.

18. Otsu, M., Yamada, M., Nakajima, S., Kida, M., Maeyama, Y., Hatano, N., Toita, N., Takezaki, S., Okura, Y., Kobayashi, R., et al. (2015). Outcomes in two Japanese adenosine deaminase-deficiency patients treated by stem cell gene therapy with no cytoreductive conditioning. J. Clin. Immunol. 35, 384-398.
19. Aiuti, A., Biasco, L., Scaramuzza, S., Ferrua, F., Cicalese, M. P., Baricordi, C., Dionisio, F., Calabria, A., Giannelli, S., Castiello, M. C., et al. (2013). Lentiviral hematopoietic stem cell gene therapy in patients with Wiskott-Aldrich syndrome. Science 341, 1233151.
20. Nakazawa, Y., Kawai, T., Uchiyama, T., Goto, F., Watanabe, N., Maekawa, T., Ishiguro, A., Okuyama, T., Otsu, M., Yamada, M., et al. (2015). Effects of enzyme replacement therapy on immune function in ADA deficiency patient. Clin. Immunol. 161, 391-393.
21. Villella, A. D., Yao, J., Getty, R. R., Juliar, B. E., Yiannoutsos, C., Hartwell, J. R., Cai, S., Sadat, M. A., Cornetta, K., Williams, D. A., and Pollok, K. E. (2005). Real-time PCR: an effective tool for measuring transduction efficiency in human hematopoietic progenitor cells. Mol. Ther. 11, 483-491.
22. Charrier, S., Ferrand, M., Zerbato, M., Precigout, G., Viornery, A., Bucher-Laurent, S., Benkhelifa-Ziyyat, S., Merten, O. W., Perea, J., and Galy, A. (2011). Quantification of lentiviral vector copy numbers in individual hematopoietic colony-forming cells shows vector dose-dependent effects on the frequency and level of transduction. Gene Ther. 18, 479-487.
23. Hindson, B. J., Ness, K. D., Masquelier, D. A., Belgrader, P., Heredia, N. J., Makarewicz, A. J., Bright, I. J., Lucero, M. Y., Hiddessen, A. L., Legler, T. C., et al. (2011). Highthroughput droplet digital PCR system for absolute quantitation of DNA copy number. Anal. Chem. 83, 8604-8610.
24. Moser, D. A., Braga, L., Raso, A., Zacchigna, S., Giacca, M., and Simon, P. (2014). Transgene detection by digital droplet PCR. PLoS ONE 9, e111781.
25. Abyzov, A., Mariani, J., Palejev, D., Zhang, Y., Haney, M. S., Tomasini, L., Ferrandino, A. F., Rosenberg Belmaker, L. A., Szekely, A., Wilson, M., et al. (2012). Somatic copy number mosaicism in human skin revealed by induced pluripotent stem cells. Nature 492, 438-442.
26. Al-Soud, W. A., and Rådström, P. (2001). Purification and characterization of PCRinhibitory components in blood cells. J. Clin. Microbiol. 39, 485-493.
27. Onodera, M., Ariga, T., Kawamura, N., Kobayashi, I., Ohtsu, M., Yamada, M., Tame, A., Furuta, H., Okano, M., Matsumoto, S., et al. (1998). Successful peripheral T-lymphocyte-directed gene transfer for a patient with severe combined immune deficiency caused by adenosine deaminase deficiency. Blood 91, 30-36.
28. Hacein-Bey-Abina, S., Garrigue, A., Wang, G. P., Soulier, J., Lim, A., Morillon, E., Clappier, E., Caccavelli, L., Delabesse, E., Beldjord, K., et al. (2008). Insertional oncogenesis in 4 patients after retrovirus-mediated gene therapy of SCID-X1. J. Clin. Invest. 118, 3132-3142.
29. Howe, S. J., Mansour, M. R., Schwarzwaelder, K., Bartholomae, C., Hubank, M., Kempski, H., Brugman, M. H., Pike-Overzet, K., Chatters, S. J., de Ridder, D., et al. (2008). Insertional mutagenesis combined with acquired somatic mutations causes leukemogenesis following gene therapy of SCID-X1 patients. J. Clin. Invest. 118, 3143-3150.
30. Braun, C. J., Bortug, K., Paruzynski, A., Witzel, M., Schwarzer, A., Rothe, M., Modlich, U., Beier, R., Göhring, G., Steinemann, D., et al. (2014). Gene therapy for Wiskott-Aldrich syndrome-long-term efficacy and genotoxicity. Sci. Transl. Med. 6, 227ra33.
31. Sadelain, M. (2004). Insertional oncogenesis in gene therapy: how much of a risk? Gene Ther. 11, 569-573.
32. Klein, A. M., Mazutis, L., Akartuna, I., Tallapragada, N., Veres, A., Li, V., Peshkin, L., Weitz, D. A., and Kirschner, M. W. (2015). Droplet barcoding for single-cell transcriptomics applied to embryonic stem cells. Cell 161, 1187-1201.
33. Onodera, M., Nelson, D. M., Yachie, A., Jagadeesh, G. J., Bunnell, B. A., Morgan, R. A., and Blaese, R. M. (1998). Development of improved adenosine deaminase retroviral vectors. J. Virol. 72, 1769-1774.
34. Ory, D. S., Neugeboren, B. A., and Mulligan, R. C. (1996). A stable human-derived packaging cell line for production of high titer retrovirus/vesicular stomatitis virus G pseudotypes. Proc. Natl. Acad. Sci. USA 93, 11400-11406.

SUMMARY OF INVENTION

Technical Problem

However, there are demands for further improvements in technique concerning the genetic characterization of a single cell.

The present invention was made in order to solve the foregoing problems, and an object of the present invention is to provide new method of amplifying a polynucleotide of interest.

Solution to Problem

In order to solve the foregoing problems, the present invention provides: a method of amplifying a target nucleic acid (polynucleotide) contained in a particle including an enclosing lipid bilayer membrane. The method includes the steps of: lysing the particle which is stored in a compartment constituted by a liquid in an amount of 100 µl or less; and amplifying the target nucleic acid in the compartment.

BRIEF DESCRIPTION OF DRAWINGS

FIG. 2A shows the structure of the retroviral vector used in this study. GCsapM-ADA was used in the clinical trials. EGFP cDNA was incorporated downstream of ADA cDNA with the sequence of an internal ribosomal entry site (IRES) in the pGCsapM-ADA-IE construct. K562 cells were transduced with GCsapM-ADA-IE to create K562-AE cells. FIG. 2B shows Direct encapsulation of K562-AE cells into droplets. The 2,000-cell samples exhibited single-cell encapsulation into droplets. Multi-cell encapsulation (triangles) and the failure of encapsulation (arrows) were observed in samples containing more than 8,000 cells. Fluorescent (EGFP) and bright-field (BF) images are shown. Scale bars represent 100 mm. FIG. 2C shows Ratios of droplets with single- or multi-cell encapsulation. Droplets were counted in 34 and 82 different fields on microscopy in the 2,000- and >8,000-cell samples, respectively. FIG. 2D shows Direct PCR subsequent to single-cell encapsulation. Droplets containing a single cell displayed fluorescent signals after amplification of the vector Ψ and reference gene RPP30. Upper panels, standard procedure; lower panels, modified procedure. LTR, long terminal repeat; SA, splice acceptor; SD, splice donor.

FIG. 3A shows Evaluation of the non-specific signals in negative samples. Target Ψ and RPP30 were amplified in mononuclear cell samples of peripheral blood (PBMCs) and cord blood from healthy donors, as well as naive K562 cells. The ratio of the target Ψ, which denotes the background signal, is shown below each sample. FIG. 3B shows Relationship between the percentages of dilution and the vector index in extracted genomic DNA from spiked cell samples. K562 cell samples were spiked with serially diluted K562-AE cells carrying the vector at a concentration of one copy per cell. Vector Ψ and RPP30 were measured using genomic DNA from spiked samples by conventional ddPCR. The vector index was calculated using the following formula: (2×number of vector-positive droplets)/(numbers of RPP30-positive droplets). An index of 1 indicates that all cells contain one copy of Ψ and two copies of RPP30 in their genomes. The measured value in each spiked sample was linearly related to the theoretical values. FIG. 3C shows Single cell-based digital droplet PCR (sc-ddPCR) using spiked samples. K562 cell samples spiked with serially diluted K562-AE cells were analyzed by sc-ddPCR. The number of Ψ signal-positive droplets, which contain vector-positive cells, declined in relationship with the spiked ratios, whereas similar numbers of RPP30-positive droplets were observed irrespective of the spiked ratio, which indicated the sample size. FIG. 3D shows Correlation between the vector index and the ratio of vector-positive droplets as determined by sc-ddPCR. sc-ddPCR was performed using spiked K562 cells, and the measured values were plotted against the vector index in genomic DNA. The ratios determined by sc-ddPCR were linearly related to the vector index.

FIG. 4A shows Immunological characterization of peripheral blood and bone marrow samples from patients via FACS analysis. Percentages of $CD3^+$ T cells, $CD56^+$ NK cells, and $CD19^+$ B cells in lymphocytes are shown in the bar chart. Bone marrow samples were also analyzed for CD34 expression. FIG. 4B shows Ratios of vector-positive cells in the whole PBMC and sorted fractions. PBMC samples from patients were sorted via FACS into $CD3^+$ T cell, $CD56^+$ NK cell, and $CD19^+$ B cell fractions, and each cell fraction and all PBMCs were encapsulated into droplets. The ratio of vector-positive cells was determined by single cell-based digital droplet PCR (sc-ddPCR). Data were pooled from three independent experiments for each patient. FIG. 4C shows Bone marrow samples after lysis of red blood cells were also sorted and analyzed for the presence of the vector Ψ sequence (whole bone marrow cells, $CD34^+$ cells). For each sample, sc-ddPCR was conducted in triplicate.

DESCRIPTION OF EMBODIMENTS

Figure 1:
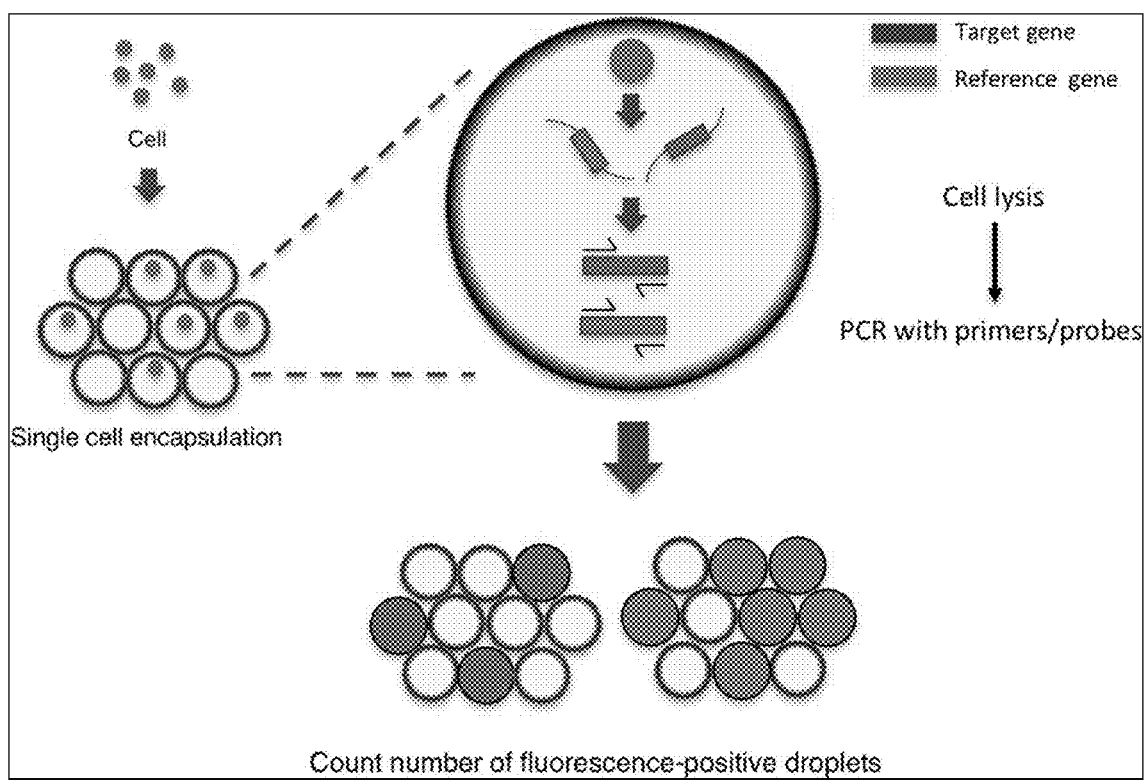
FIG. 1 shows a schematic of the Single Cell-Based Digital Droplet PCR System. Cells from the target population were encapsulated into droplets at a concentration of one cell/droplet with the PCR mixture including primers and probes. After single-cell encapsulation, cell lysis and amplification of the target sequence were performed within the droplets. The number of droplets with a fluorescent signal indicates the number of cells carrying the target or reference gene. sc-ddPCR, single cell-based digital droplet PCR.

The following will describe an embodiment of the present invention in detail.

The present invention encompasses the following aspects.

(1) A method of amplifying a target nucleic acid (polynucleotide) contained in a particle including an enclosing lipid bilayer membrane, including the steps of: lysing the particle which is stored in a compartment constituted by a liquid in an amount of 100 μl or less (preferably 50 μl or less, more preferably 40 μl or less, still more preferably 15 μl to 35 μl or 15 μl to 25 μl); and amplifying the target nucleic acid in the compartment.

(2) The method described in (1), in which the compartment is a droplet.

(3) The method described in (1) or (2), in which the particle is a cell or a liposome.

(4) The method described in (1) or (2), in which the particle is a cell preparation or a liposome preparation.

(5) The method described in any one of (1) through (4), in which the particle is a stem cell (such as a cell for regenerative medicine or a cancer stem cell) or a cell (such as a cell for regenerative medicine or a cancer stem cell) derived from the stem cell.

(6) The method described in (5), in which the stem cell is an induced pluripotent stem cell (iPS cell) or a cell derived from the induced pluripotent stem cell.

(7) The method described in any one of (1) through (5), in which the particle is a cell (such as a group of normal cells or a mixed group of a normal cell and an abnormal cell (such as a cancer cell)) collected from a living body. The cell collected from the living body can be, for example, a cell collected from a human or a cell collected from a human patient. However, the present invention is not particularly limited to these examples.

(8) The method described in any one of (1) through (7), in which the particle contains, as the target nucleic acid, a nucleic acid for gene therapy.

(9) The method described in any one of (1) through (6), in which the particle contains, as the target nucleic acid, a genetically recombinant nucleic acid.

(10) The method described in any one of (1) through (9), in which the liquid contains an active component (such as an active component contained in a cell lysis solution or in a cell lysis buffer) for lysing the particle.

(11) The method described in (10), in which the liquid contains a surfactant (such as an anionic surfactant, a cationic surfactant, a nonionic surfactant, or an amphoteric surfactant) as the active component. Examples of the anionic surfactant encompass, but are not particularly limited to, sodium dodecyl sulfate SDS. Examples of the nonionic surfactant encompass, but are not particularly limited to, fatty acid surfactants such as polyoxyethylene sorbitan monolaurate, polyoxyethylene sorbitan monopalmitate, polyoxyethylene sorbitan monostearate, and polyoxyethylene sorbitan monooleate; higher alcohol surfactants such as polyvinyl alcohol; and alkylphenol surfactants such as polyoxyethylene octylphenyl ether. Examples of the amphoteric surfactant encompass 3-[(3-cholamidepropyl)dimethylammonio]-1-propanesulfonate (CHAPS).

(12) The method described in (11), in which the surfactant is contained at a concentration which falls within a range of 0.005% (w/v) or more and 0.1% (w/v) or less (preferably 0.01% (w/v) or more and 0.05% (w/v) or less, more preferably 0.01% (w/v) or more and 0.025% (w/v) or less, and still more preferably 0.01% (w/v) or more and 0.02% (w/v) or less).

(13) The method described in any one of (10) through (12), in which the active component is contained in the liquid at a concentration at which the compartment (such as a droplet) is not disrupted. The range of the concentration defined in (12) above is an example of the concentration at which the compartment (such as a droplet) is not disrupted.

(14) The method described in any one of (10) through (13), in which the active component is contained in the liquid at a concentration at which the particle is lysed under an additional operation for lysing the particle.

(15) The method described in (14), in which the additional operation is heating. A time period in which the heating is performed is, for example, not less than 1 minute, not less than 10 minutes, not less than 30 minutes, not less than 40 minutes, or not less than 50 minutes. However, the present invention is not particularly limited to these examples. An upper limit of the time period in which the heating is performed is not particularly limited. However, it is unnecessary to continue the heating after the particle has been sufficiently lysed. The time period is, for example, not more than 150 minutes, not more than 120 minutes, not more than 90 minutes, or not more than 80 minutes.

(16) The method described in (15), in which the heating is carried out to raise a temperature to 40° C. or higher (preferably 50° C. or higher, 55° C. or higher, 60° C. or higher, 65° C. or higher, 70° C. or higher, 75° C. or higher, 80° C. or higher, or 85° C. or higher). Note that the temperature during the heating may be preferably less than 100° C., may be more preferably not higher than 95° C., or may be still more preferably not higher than 90° C.

(17) The method described in (15) or (16), in which the heating is carried out immediately before the amplifying of the target nucleic acid or carried out as a step involved in an operation for the amplifying of the target nucleic acid.

(18) The method described in any one of (1) through (17), in which a desired number of particles (preferably cells) are stored in each of 70% or more (preferably 75% or more, 80% or more, 85% or more, 90% or more, or 95% or more) of the compartments.

(19) The method described in (18), in which the desired number of particles is one.

(20) The method described in any one of (2) through (19), in which the droplet in which a desired number of particles (preferably cells) are stored is formed from the liquid containing a plurality of the particles (preferably cells).

(21) The method described in (20), in which the droplet is formed as a droplet of water in oil.

(22) The method described in (20) or (21), in which the liquid contains the particles (preferably cells) at a concentration of $2\times10^5$ particles/ml or less (preferably $1.5\times10^5$ particles/ml or less, more preferably in a range of $1.5\times10^4$ particles/ml or more and $1.5\times10^5$ particles/ml or less, and still more preferably in a range of $5\times10^4$ particles/ml or more and $1.5\times10^5$ particles/ml or less).

(23) The method described in any one of (20) through (22), in which a desired number of cells are stored in each of 70% or more (preferably 75% or more, 80% or more, 85% or more, 90% or more, or 95% or more) of the droplets.

(24) The method described in any one of (20) through (23), in which the desired number of cells is one.

(25) The method described in any one of (20) through (24), in which the droplet is prepared by use of a droplet generator (such as a droplet generator for preparing a droplet for use in droplet digital PCR).

(26) The method described in any one of (1) through (25), in which the amplifying of the target nucleic acid is carried out by PCR (preferably hot start PCR). The conditions for the PCR can be determined according to an ordinary method, and can be determined by, for example, referring as appropriate to conditions which are typically employed in digital droplet PCR. The following are examples of the conditions. However, the present invention is not particularly limited to these examples.

A) Each set of primers is contained in a PCR reaction solution (i.e., the droplet) at a concentration of, for example, preferably in a range of 0.3 µM to 0.7 µM, more preferably in a range of 0.4 µM to 0.6 µM, and still more preferably in a range of 0.45 µM to 0.55 µM.

B) A GC content of the primer is, for example, preferably in a range of 50% to 70%, and more preferably in a range of 50% to 65%.

C) A Tm value of the primer is preferably 50° C. to 65° C., and more preferably 50° C. to 60° C.

Note that by a person skilled in the art, a sequence of the primer (including a length of the sequence) can be designed according to (i) a sequence of a target nucleic acid to be amplified and (ii) the common technical knowledge of the technical field concerned.

D) The number of PCR cycles is, for example, in a range of 30 times to 60 times, or in a range of 30 times to 50 times. Alternatively, the number of PCR cycles can be, for example, in a range of 35 times to 50 times, or in a range of 40 times to 50 times.

E) An annealing temperature is preferably 58° C. to 64° C., and more preferably approximately 60° C.

F) An amount of DNA polymerase (preferably Hot Start DNA polymerase) in the PCR reaction solution (i.e., the droplet) can be approximately 0.9 units/droplet (20 µl) to 1.1 units/droplet (20 µl). Note, however, that the amount may be preferably more than such an amount, such as approximately 5 times or more, approximately 10 times or more, approximately 20 times or more, approximately 30 times or more, approximately 40 times or more, or approximately 45 times as much. This is because in a case where a cell or the like contained in the droplet is lysed, a component which inhibits a PCR reaction may be mixed into the reaction solution.

G) In a case where a visualization probe (which binds to an amplified fragment obtained in PCR amplification) is to be used in order to detect the amplified fragment, the visualization probe is to be contained in the PCR reaction solution (i.e., the droplet) at a concentration of, for example, preferably in a range of 0.3 µM to 1.3 µM, more preferably in a range of 0.4 µM to 1.2 µM, and still more preferably in a range of 0.45 µM to 1.1 µM.

(27) The method described in any one of (1) through (26), in which the liquid contains a composition (including, for example, a primer (such as a PCR primer set) for amplifying a nucleic acid, an enzyme (such as a DNA polymerase) for amplification, a dNTP mix, and, as necessary, a visualization probe (fluorescent probe) which binds to an amplified fragment, and a visualization intercalator (fluorescent intercalator) to be inserted into an amplified fragment) for amplifying the target nucleic acid.

(28) The method described in any one of (1) through (27), in which the target nucleic acid to be amplified is a nucleic acid for gene therapy or a genetically recombinant nucleic acid. In this case, a nucleic acid sequence of a vector used for genetic recombination can be a sequence to be amplified or a sequence to be annealed by a primer).

(29) The method described in any one of (1) through (28), in which the target nucleic acid to be amplified is a DNA in a genome contained in a cell serving as the particle or is a DNA in a cytoplasm contained in a cell serving as the particle.

(30) The method described in any one of (1) through (28), in which the target nucleic acid to be amplified is a marker nucleic acid characterizing a cell containing the target nucleic acid.

(31) The method described in (30), in which the marker nucleic acid characterizes an abnormal cell (such as a cancer stem cell or various cancer cells). That is, the marker nucleic acid can be a cancer marker or the like.

(32) The method described in any one of (1) through (31), in which: a result of the amplifying of the target nucleic acid in each compartment is visualized; and the result is read by a reader.

(33) The method described in (32), in which the result of the amplifying of the target nucleic acid is visualized through whether or not there is emission of fluorescence.

(34) The method described in (32) or (33), in which the result is visualized and read by a droplet digital PCR technique.

(35) The method described in any one of (1) through (34), further including the step of: detecting, on the basis of a result of amplifying of a target nucleic acid(s), 1) a ratio of a particle(s) (preferably a cell or a liposome) containing the target nucleic acid(s) or 2) presence/absence of a particle(s) (preferably a cell(s) or a liposome(s)) containing the target nucleic acid(s). The method further includes, for example, the step of evaluating a quality of a particle(s) or identifying a type(s) of a particle(s) on the basis of the result of the detecting.

(36) The method described in any one of (1) through (35), further including the step of: evaluating, on the basis of a result of amplifying of the target nucleic acid, a quality of the particle (preferably a cell or a liposome) including the enclosing lipid bilayer membrane.

(37) The method described in any one of (1) through (27), further including the step of: identifying, on the basis of a result of the amplifying of the target nucleic acid, a type of a cell serving as the particle including the enclosing lipid bilayer membrane.

(38) The method described in (37), in which the identifying of the type of the cell is distinguishing between an abnormal cell (such as a cancer cell) and a normal cell.

(39) A method of amplifying a target nucleic acid contained in a cell, including the steps of: lysing the cell which is stored in a droplet; and amplifying the target nucleic acid in the droplet.

(40) A kit for carrying out the method described in any one of (1) through (39) is also an aspect of the present invention. This kit includes, for example, at least one of the following 1) through 4) to be contained in the compartment (preferably a droplet) in which the particle (preferably a cell or a liposome) is stored and which is constituted by a liquid in an amount of 100 µl or less. The kit preferably includes all of the following 1) through 4).

1) a surfactant, 2) a composition (for example, a primer for amplifying a nucleic acid, such as a PCR primer set) for amplifying a target nucleic acid, 3) an enzyme (such as a DNA polymerase) for amplification, and 4) a dNTP mix.

(41) The kit described in (40) can further include, as necessary, a visualization probe (fluorescent probe) which binds to an amplified fragment, and/or a visualization intercalator (fluorescent intercalator) to be inserted into an amplified fragment.

(42) The kit described in (40) or (41) further includes a kit instruction manual for carrying out the method described in any one of (1) through (39).

This application claims priority on the U.S. provisional application No. 62/675,888 which was filed on May 24, 2018. The following are hereby incorporated by reference (IBR): (i) the entire content of the U.S. provisional application No. 62/675,888, (ii) the Non-Patent Literature (Title: "Single Cell-Based Vector Tracing in Patients with ADA-SCID Treated with Stem Cell Gene Therapy". Molecular Therapy: Methods & Clinical Development Vol. 6, p 8-, September 2017) corresponding to the U.S. provisional application No. 62/675,888, and (iii) the entire contents of the Non-Patent Literatures cited herein.

EXAMPLE

The following will further specifically describe the present invention with reference to Examples, Comparative Examples, etc. below. However, the present invention is not limited to these.

Summary of Examples

Clinical improvement in stem cell gene therapy (SCGT) for primary immunodeficiencies depends on the engraftment levels of genetically corrected cells, and tracing the transgene in each hematopoietic lineage is therefore extremely important in evaluating the efficacy of SCGT. Inventors established a single cell-based droplet digital PCR (sc-ddPCR) method consisting of the encapsulation of a single cell into each droplet, followed by emulsion PCR with primers and probes specific for the transgene. A fluorescent signal in a droplet indicates the presence of a single cell carrying the target gene in its genome, and this system can clearly determine the ratio of transgene-positive cells in the entire population at the genomic level. Using sc-ddPCR, inventors analyzed the engraftment of vector-transduced cells in two patients with severe combined immunodeficiency (SCID) who were treated with SCGT. Sufficient engraftment of the transduced cells was limited to the T cell lineage in peripheral blood (PB), and a small percentage of CD34$^+$ cells exhibited vector integration in bone marrow, indicating that the transgene-positive cells in PB might have differentiated from a small population of stem cells or lineage-restricted precursor cells. sc-ddPCR is a simplified and powerful tool for the detailed assessment of transgene-positive cell distribution in patients treated with SCGT.

Introduction

Stem cell-based gene therapy has been proposed as a highly desirable treatment for primary immunodeficiencies (PIDs) when patients lack human leukocyte antigen (HLA)-matched suitable donors for hematopoietic stem cell transplantation (HSCT). The addition of the therapeutic gene to autologous hematopoietic stem cells (HSCs) is an attractive alternative because the gene-corrected HSCs are expected to reconstitute the functional immune system in the same manner as allogeneic HSCs in treated patients (Non-Patent Literatures 1-4). A series of HSCbased gene therapy clinical trials confirmed this expectation, revealing that treated patients displayed multi-lineage expression of the transduced gene (Non-Patent Literatures 5-12).

To achieve clinical improvement, sufficient engraftment of the transduced cells is required, although various factors, including the selective advantage of the therapeutic gene, affect their engraftment in bone marrow (BM) (Non-Patent Literatures 5, 6, 10-12). Therefore, the mapping of gene-transduced cell distributions in treated patients is required to evaluate the efficacy of gene therapy. Recently, advances in the genetic characterization of a single cell provided insights into genomic and transcriptomic heterogeneity (Non-Patent Literature 13), and such insights can be helpful in the field of gene therapy.

In this study, inventors developed a single cell-based droplet digital PCR (scddPCR) system consisting of single-cell encapsulation, droplet PCR using a fluorescent probe, and the detection of signal-positive droplets. This novel strategy enables direct detection of the vector sequence at the genomic level in each cell of the target population. Using the established method, inventors analyzed gene therapy-treated patients with adenosine deaminase (ADA)-deficient severe combined immunodeficiency (SCID), which is caused by mutation of the ADA gene. ADA is important for the purine metabolic pathway, and genetic defects in the ADA gene result in autosomal recessive type SCID (Non-Patent Literature 14). For patients without suitable HSCT donors, enzyme replacement therapy with polyethylene glycol-modified bovine ADA (PEG-ADA) is a widely used treatment option worldwide (Non-Patent Literature 15). However, PEG-ADA therapy often results in partial immune reconstitution (Non-Patent Literature 16), and gene therapy using autologous HSCs has been studied as an alternative curative treatment for those patients (Non-Patent Literature 6).

In current gene therapy approaches for ADA deficiency, withdrawal of PEG-ADA and preconditioning treatment with busulfan are indispensable for achieving full engraftment of gene-transduced cells in all hematopoietic lineages (Non-Patent Literatures 6, 9, 17). In 2015, inventors reported two patients with ADA-SCID who were treated with retrovirus-mediated gene therapy (Non-Patent Literature 18). Although PEG-ADA replacement was withdrawn in our trial, the patients never received preconditioning chemotherapy before the transplantation of gene-modified HSCs; therefore, partial and temporal reconstitution of the immune system was observed in both patients.

Our sc-ddPCR method allowed us to assess the detailed distribution of the vector-containing cells in peripheral blood (PB) and BM and revealed the skewed engraftment of gene-transduced cells in the hematopoietic systems of these patients.

Example 1

Results
Single-Cell Encapsulation into a Droplet

Figure 2A:
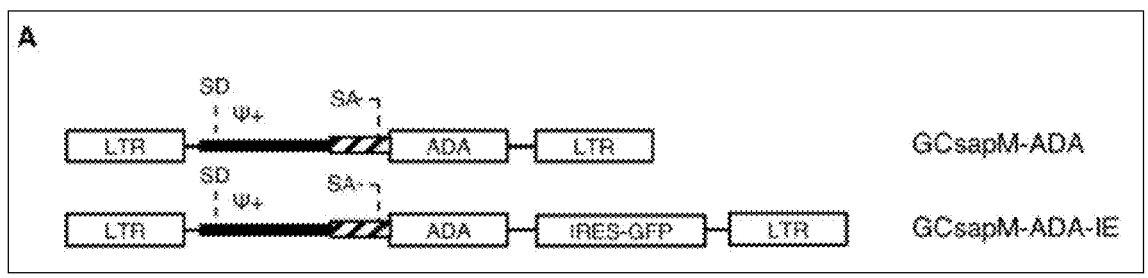
FIG. 2A, FIG. 2B, FIG. 2C, and FIG. 2D show Single-Cell Encapsulation and Direct PCR.

The sc-ddPCR system commenced with the encapsulation of a single cell into one droplet and then proceeded to the step of PCR using a TaqMan hydrolysis probe, followed by detection of the fluorescent signal in the droplets (FIG. 1). K562 cells were transduced with a retroviral vector expressing ADA and EGFP (FIG. 2A). Cell clones with single copy integration, which enabled us to trace vector integration via EGFP expression, were used for the following experiments (K562-AE cells).

Figure 2B:
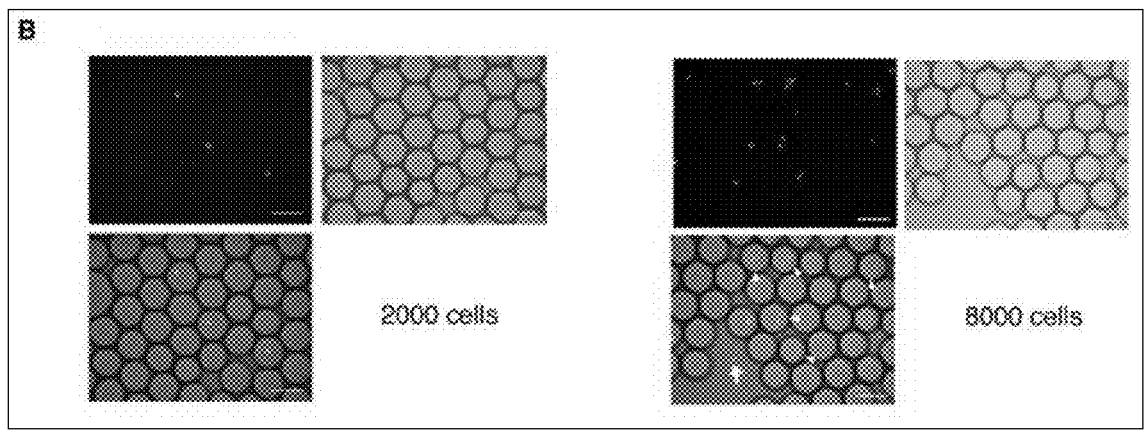
Figure 2C:
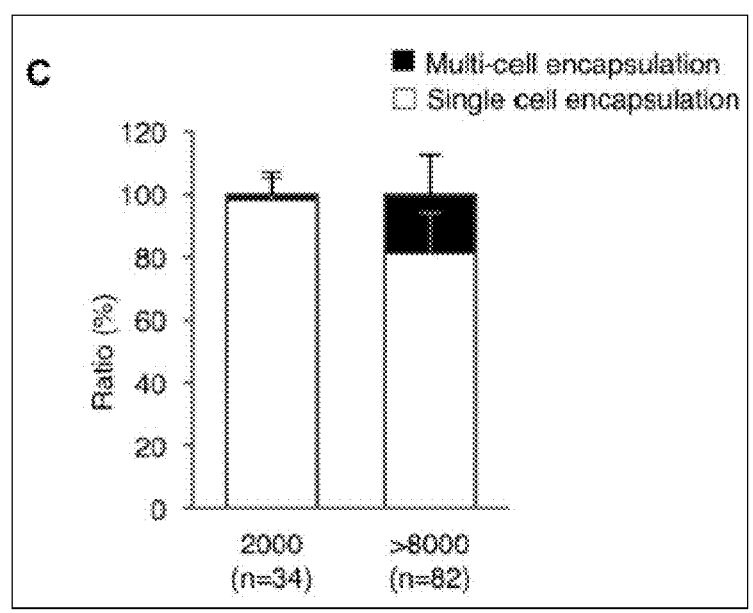
Figure 6:
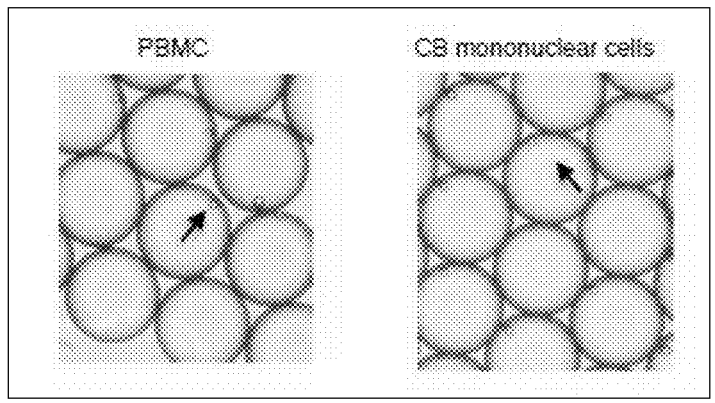
FIG. 6 shows Single-cell encapsulation of PBMCs and CB mononuclear cells.

Inventors added various numbers of K562-AE cells to the standard PCR reaction directly and generated droplets using the QX200 system's droplet generator. The 2,000-cell samples were successfully encapsulated into droplets, and single-cell encapsulation was observed in 98% of the cell-containing droplets (FIG. 2B and FIG. 2C). However, samples containing more than 8,000 cells displayed multi-cell encapsulation, and several cells were located outside the droplets. Inventors also confirmed that single-cell encapsulation is not influenced by cell type, based on the result of 2,000-cell encapsulation using PB mononuclear cells (PBMCs) and cord blood mononuclear cells (FIG. 6).

Direct PCR Inside Droplets

Figure 2D:
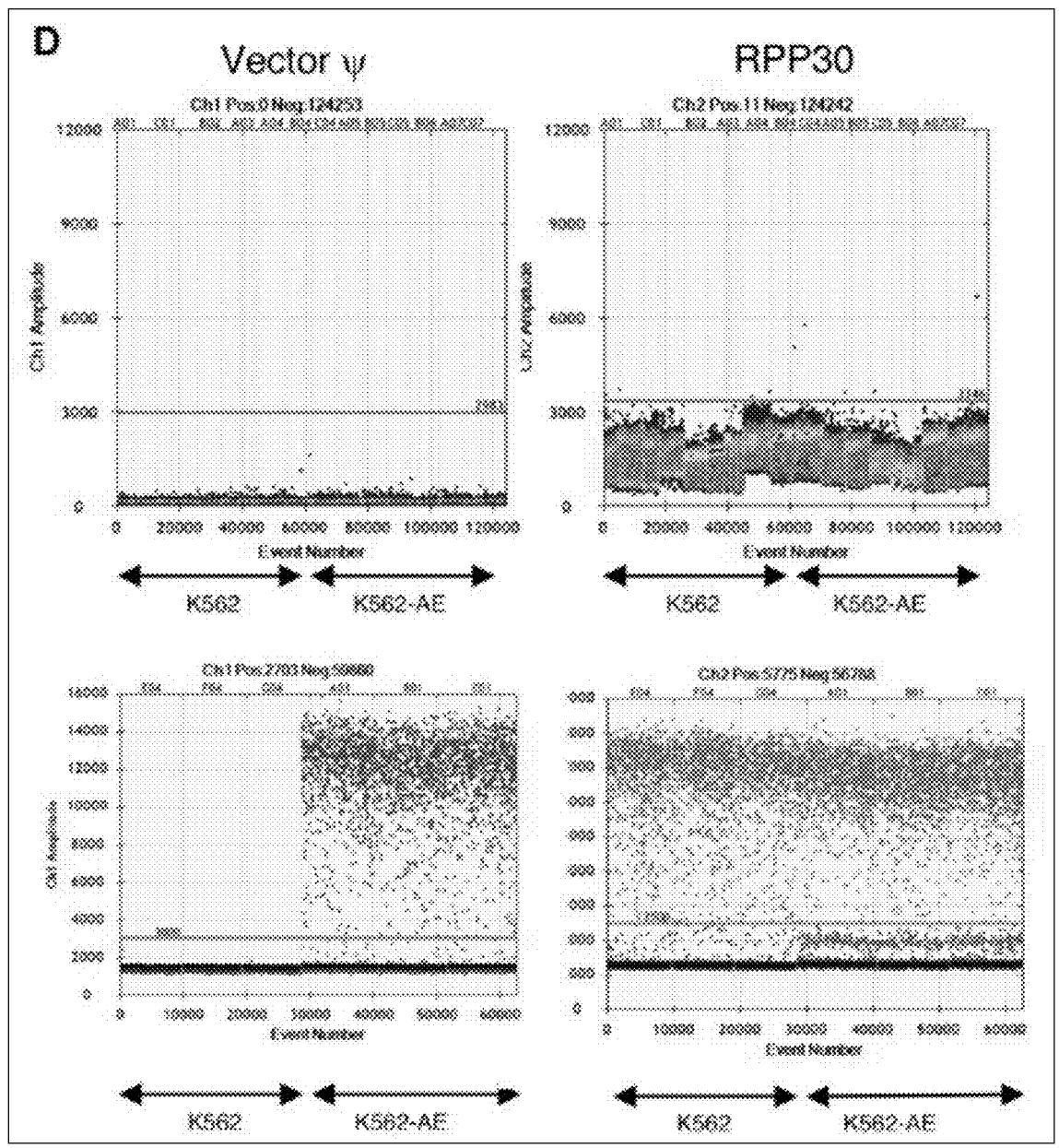

Direct PCR subsequent to cell encapsulation requires cell lysis within each droplet to amplify the target sequence in the genome. PCR using a standard composition of solution mix and a standard program did not produce any signals in the droplets, which indicated the failure of cell lysis inside the droplet (FIG. 2D, upper panels). Therefore, inventors added additional SDS to the reaction, and as part of the cell lysis step, inventors incorporated preheating at 85° C. into the PCR program. To amplify the target gene in the presence of undesirable substances such as inhibitors from lysed cells, inventors further added DNA polymerase to the reaction (Tables 3 and 4). After these modifications, clear fluorescent signals were observed in the droplets (FIG. 2D, lower panels), and this high fluorescent amplitude of vector $\Psi$ and RPP30 was sufficient to permit separation from that of negative samples. The fluorescent signal in each droplet directly indicated the existence of a cell carrying the vector inside the droplet.

Assessment of the Detection Capability of sc-ddPCR

Figure 3A:
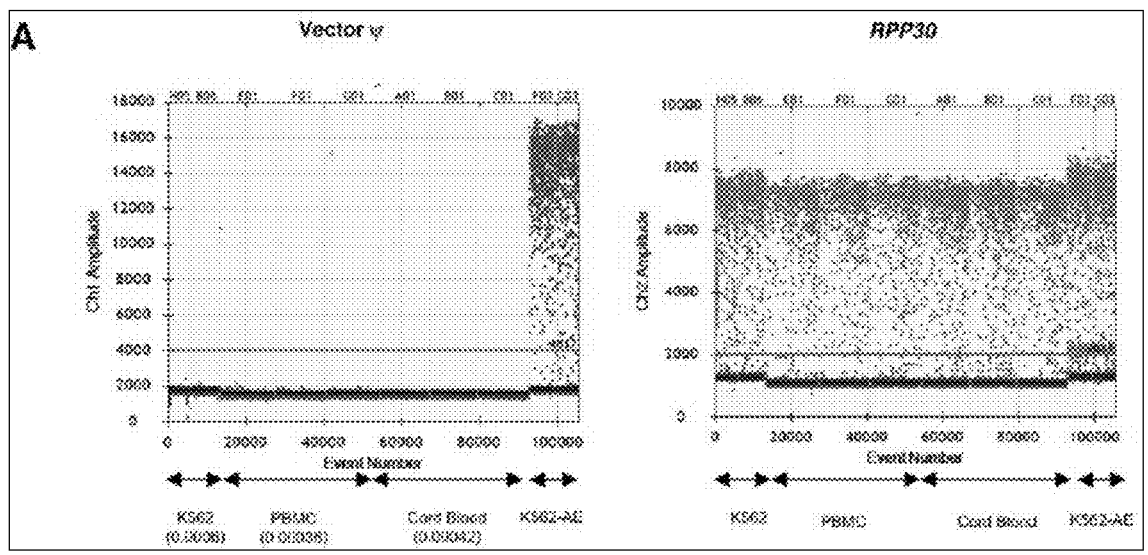
FIG. 3A, FIG. 3B, FIG. 3C, and FIG. 3D show Estimation of the Accuracy of Single Cell-Based Digital Droplet PCR.

Inventors first estimated the accuracy of the sc-ddPCR system's detection capability using K562-AE cells. Non-specific vector signals in negative samples could lead to overestimation of the frequency of vector-positive cells. An extremely low vector signal could be observed in non-transduced K562 cells (vector $\Psi$/RPP30=0.0006) as well as PBMCs and cord blood $CD34^+$ cells (vector $\Psi$/RPP30=0.00036 and 0.00042, respectively) (FIG. 3A). Inventors concluded that the level of false positivity due to non-specific vector signals was minimal. Multi-cell encapsulation may decrease the number of signal-positive droplets because, for example, two to three cells encapsulated in one droplet are calculated as "one cell" in sc-ddPCR. To evaluate the influence of multi-cell encapsulation, inventors analyzed 10,000- or 20,000-cell samples by encapsulating the cells in one reaction or dividing the cells into reactions with 2,000 cells each. Encapsulation of the cells into one reaction resulted in a lower number of signals due to multi-cell encapsulation (FIG. 7), which revealed the importance of single-cell encapsulation for accurate evaluation.

Figure 3B:
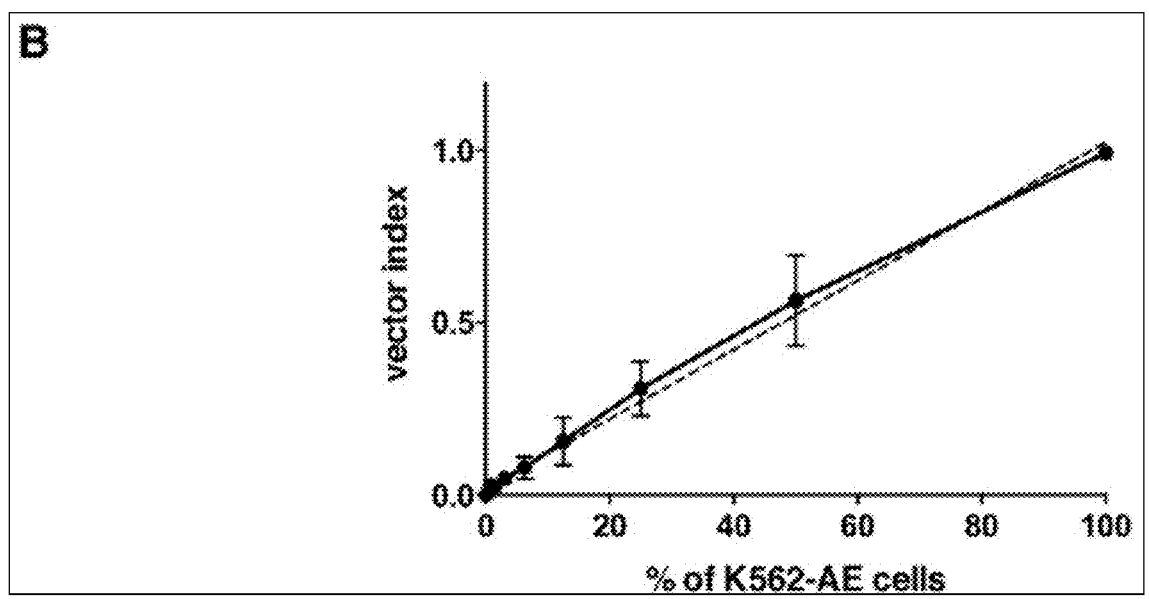
Figure 3C:
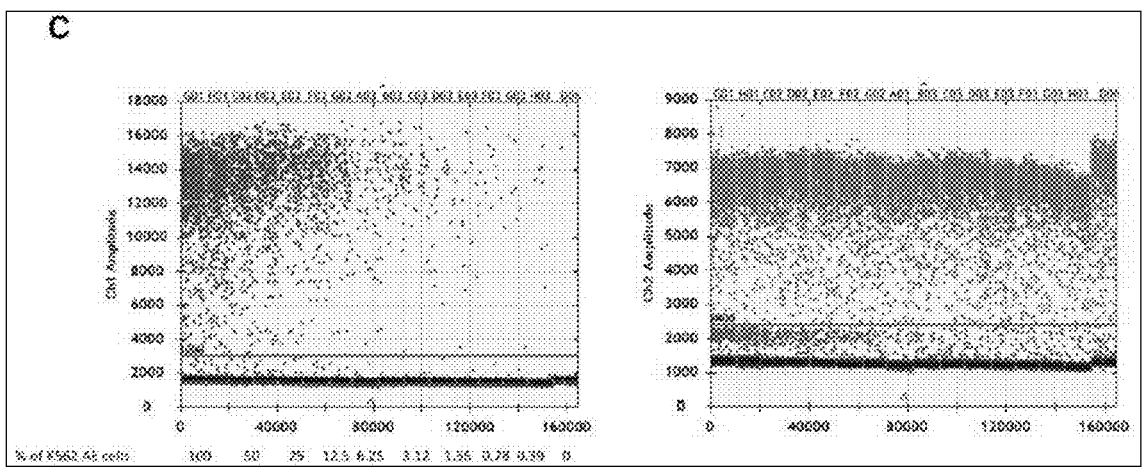
Figure 3D:
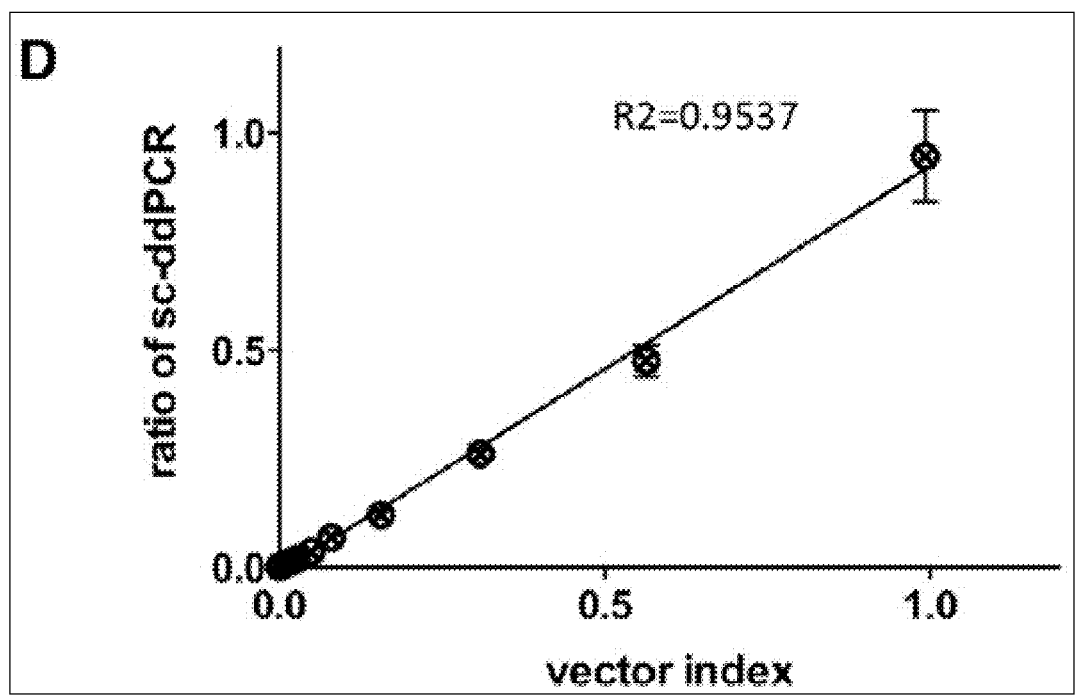

Inventors then examined whether sc-ddPCR could clarify the ratios of target cells among the populations. Naive K562 cells were spiked with one-copy K562-AE cells at serially diluted ratios. Using genomic DNA extracted from each sample, inventors analyzed the levels of the vector $\Psi$ sequence and internal reference gene RPP30 using the ddPCR system and calculated the vector index as described in the Materials and Methods. The determined index indicated the actual ratios of the serial dilution at the genomic level in the spiked cell samples (FIG. 3B). These spiked samples were then enclosed into droplets at 2,000 cells per reaction, and sc-ddPCR was performed with the modified protocol for detecting vector $\Psi$ and RPP30. The fluorescent signal in each droplet indicated the presence of a cell containing the target sequence in its genome (FIG. 3C). The ratio of vector-positive cells was calculated as follows: vector-positive ratio=(number of vector-positive droplets)/(number of RPP30-positive droplets). The signal for RPP30 denotes the sample size; therefore, the droplet numbers were always constant among the spiked samples. Meanwhile, the ratio of droplets positive for vector Ψ deteriorated consistent with the pre-designed proportion of K562-AE cells in each sample (FIG. 3C). In each spiked sample, the ratio of vector-positive cells according to sc-ddPCR significantly corresponded to the vector index in extracted genomic DNA at levels ≥0.004 (FIG. 3D; Table 1). These data revealed that sc-ddPCR enabled direct detection of the provirus sequence in cells without DNA extraction.

TABLE 1

Comparison of the Vector Index of Genomic DNA and Ratios of Vector-Positive Cells

Figure 4A:
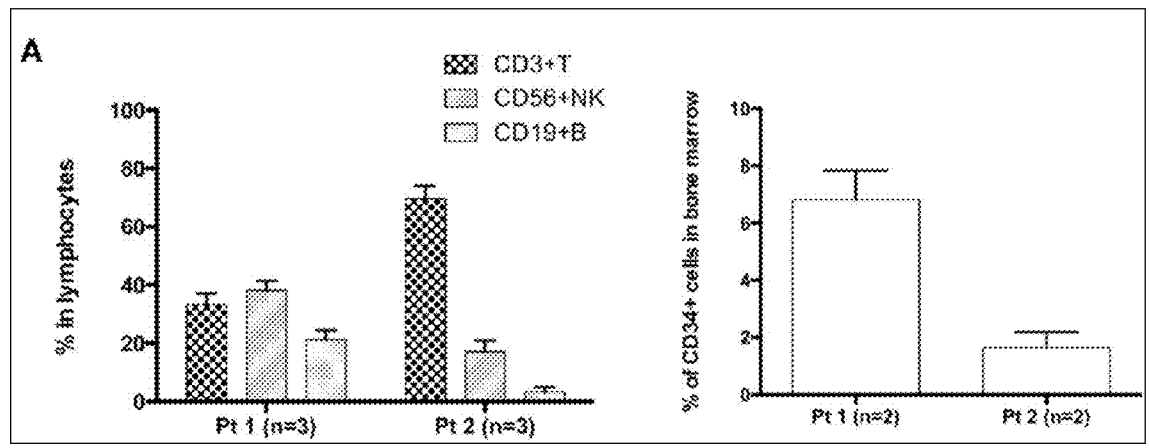
FIG. 4A, FIG. 4B, and FIG. 4C show Droplet-Based Single-Cell PCR Analysis of Peripheral Blood and Bone Marrow Samples from Patients. Droplet-based single-cell PCR (dsPCR) was performed using samples from two patients.
Figure 4B:
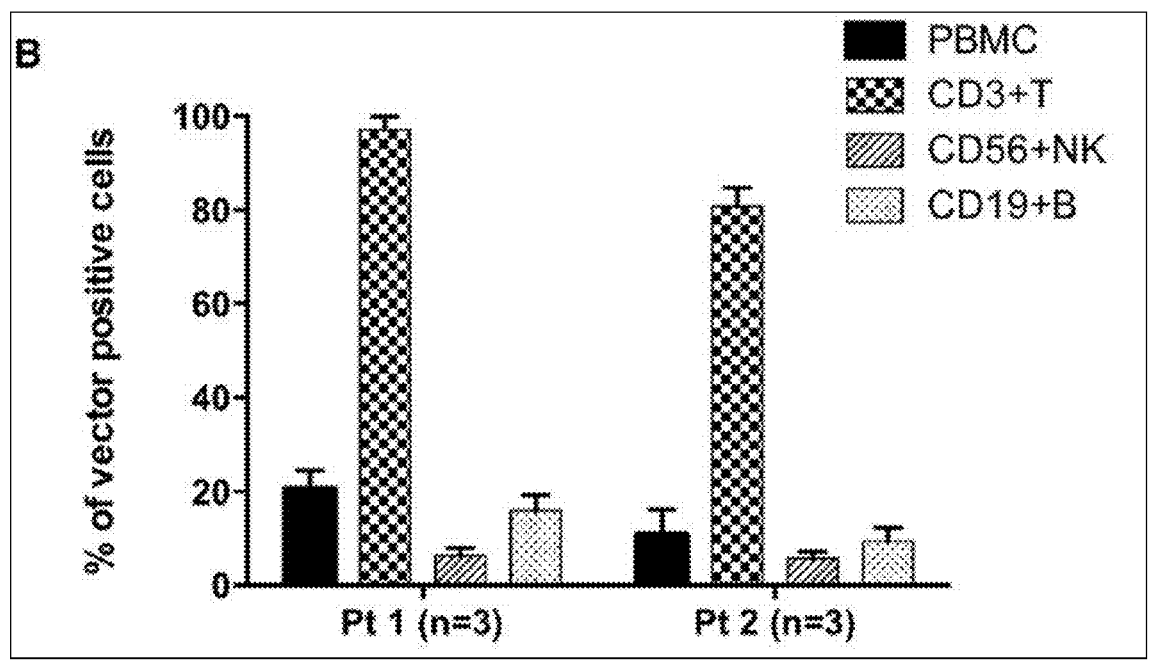
Figure 4C:
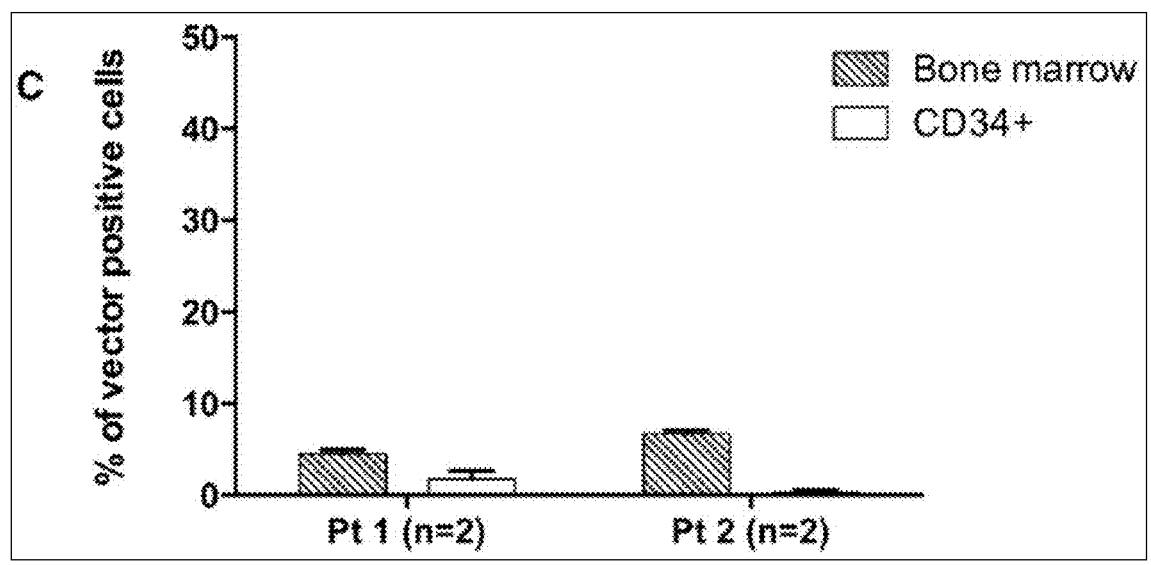
Figure 8:
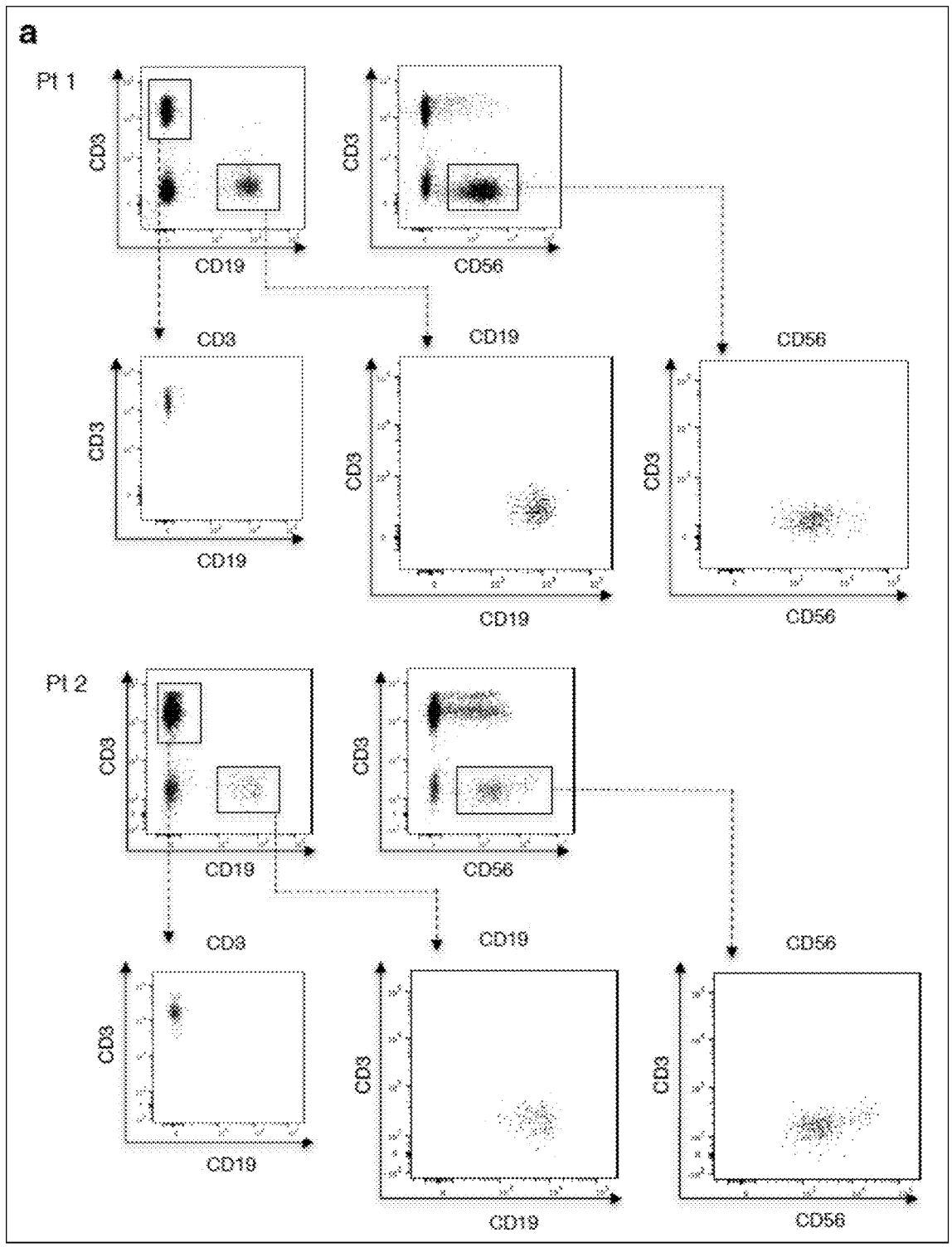
FIG. 8 shows Purity of FACS-sorted fractions of patient cells.

| Vector Index on gDNA[a] | Ratio of sc-ddPCR |
|---|---|
| 0.992 | 0.954 |
| 0.564 | 0.475 |
| 0.304 | 0.261 |
| 0.156 | 0.12 |
| 0.079 | 0.068 |
| 0.049 | 0.035 |
| 0.026 | 0.018 |
| 0.017 | 0.018 |
| 0.004 | 0.004 |
| 0 | 0.0006 | gDNA, genomic DNA.
[a]The vector index was calculated with the following formula using extracted genomic DNA: (2 × number of vector-positive droplets)/(number of RPP30-positive droplets).

sc-ddPCR Revealed Skewed Engraftment of Hematopoietic Lineages in Gene Therapy-Treated Patients Using this novel system, inventors then analyzed two patients with ADA-SCID treated with stem cell gene therapy (SCGT) using the retroviral vector GCsapM-ADA in 2003 and 2004, respectively. Patient characterization and a summary of the treatment were previously reported. Briefly, administration of PEG-ADA for both patients was discontinued 5 weeks prior to harvesting BM. The doses of CD34$^+$ cells administered were 1.38×10$^6$ cells/kg for patient 1 (Pt1) and 0.92×10$^6$ cells/kg for patient 2 (Pt2), with transduction efficiencies of approximately 40% and 50%, respectively. Neither patient previously received cytoreductive treatments such as busulfan before the manipulated cells were infused; therefore, they experienced partial improvements in immune system function, in addition to improvements of their clinical courses. The current immunological and hematological characterization of the patients is shown in FIG. 4A. Although the existence of three lymphocyte lineages (CD3$^+$ T cells, CD19$^+$ B cells, and CD56$^+$ natural killer [NK] cells) in PB was observed in Pt1, the B lymphocyte lineage was markedly reduced in Pt2. In BM, the proportions of CD34$^+$ subset that contained hematopoietic repopulating cells were 6.8% (Pt1) and 1.7% (Pt2). Detailed information about the number of lymphocytes in PB and nucleated cells in BM are described in the Supplemental Information.

sc-ddPCR analysis was then performed for both patients. PBMCs corrected from patients were sorted into CD3$^+$ T cell, CD56$^+$ NK cell, and CD19$^+$ B cell subsets by fluorescence-activated cell sorting (FACS) and then enclosed in the droplets. In sc-ddPCR analysis, almost all of the existing CD3$^+$ T cells exhibited vector integration in the genome (97.1% in Pt1 and 80.8% in Pt2), whereas only some CD56$^+$ NK and CD19$^+$ B cells displayed vector integration (FIG. 4B). The possibility of false positivity in B and NK cells due to the contamination of T cells was eliminated by checking the purity of the sorted cells (FIG. 8). These results indicated that ADA-positive T cells have a strong growth advantage over non-transduced cells. In the BM of Pt1, the entire nucleated cell population and a fraction of CD34$^+$ cells exhibited extremely low levels of vector integration (FIG. 4C). Pt1 displayed vector integration in 4.5% of all nucleated cells and 1.73% of CD34$^+$ cells. Although Pt2 had a higher ratio of vector integration in all nucleated cells (6.6%), the patient's CD34$^+$ cells displayed no vector integration. Based on these results, both patients displayed long-standing engraftment of gene-transduced HSCs in BM at a remarkably low level.

Calculation of Vector Copy Numbers in the Population of Gene-Transduced Cells

Inventors also determined the vector copy number (VCN) restricted to the fraction of transduced cells (tVCN) of the target population based on the ratio of vector-positive cells by sc-ddPCR and the average copy number in genomic DNA (aVCN) via conventional ddPCR, as described in the Materials and Methods. For the preliminary experiment using cell lines, inventors also prepared K562 cell clones with various numbers of copies (one, two, four, and five) of the vector sequence. K562 cell samples serially diluted with these cells were assayed regarding the ratio of vector-positive cells and the aVCN by sc-ddPCR and conventional ddPCR, respectively. In most spiked samples, the copy number was almost correctly calculated on the basis of these measured values in accordance with the pre-determined actual copy numbers (Table 6).

Figure 5:
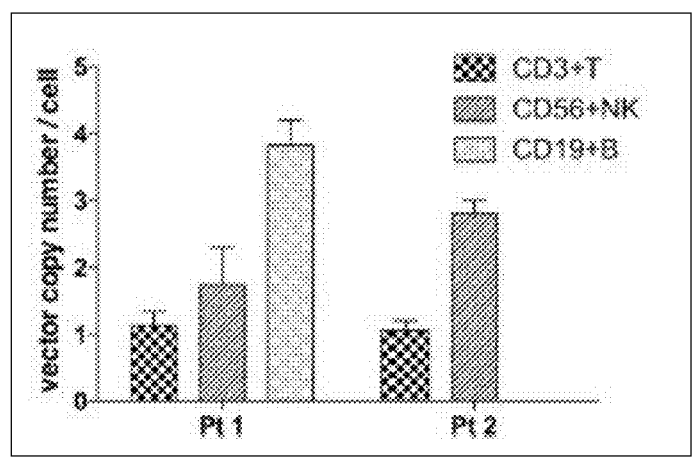
FIG. 5 shows Difference in Vector Copy Numbers in Gene-Transduced Cells between T Cell and Other Hematopoietic Lineages. Vector copy numbers (VCNs) in gene-transduced cells (tVCNs) were calculated for $CD3^+$ T cells, $CD19^+$ B cells, and $CD56^+$ NK cells. The transduced cells displayed greater VCNs in B and NK cells compared to the value of approximately 1 in T cells (two independent experiments for each patient).

Using this method, inventors measured the tVCNs in the sorted fractions from PBMCs and BM. Interestingly, in the PBMC samples, whereas T cells displayed the integration of approximately one copy, more integrated vectors were detected in the vector-positive fractions from B and NK cells (FIG. 5; Table 2). These results revealed that lower numbers of integrated vectors could provide a selective advantage to T cells, whereas B and NK cells, even with greater vector integration, could not expand predominantly over the non-transduced cells.

TABLE 2

Vector Copy Numbers Limited to Transduced Cells in the Peripheral Blood and Bone Marrow Samples from Gene Therapy-Treated Patients

| | Peripheral Blood (Third Sample) | | | Bone Marrow | | |
|---|---|---|---|---|---|---|
| | T Cell | B Cell | NK Cell | Whole | CD34$^+$ | CD19$^+$ |
| Patient 1 | | | | | | |
| VCN in gDNA (aVCN) | 1.34 | 0.84 | 0.16 | 0.06 | ND[b] | 0.04 |
| Ratio by sc-ddPCR | 1.00[a] | 0.20 | 0.71 | 0.049 | 0.027 | 0.011 |
| VCN/cell (tVCN) | 1.34 | 4.2 | 2.3 | 1.2 | ND | 3.5 |

TABLE 2-continued

Vector Copy Numbers Limited to Transduced Cells in the Peripheral Blood and Bone Marrow Samples from Gene Therapy-Treated Patients

| | Peripheral Blood (Third Sample) | | | Bone Marrow | | |
|---|---|---|---|---|---|---|
| | T Cell | B Cell | NK Cell | Whole | CD34+ | CD19+ |
| Patient 2 | | | | | | |
| VCN in gDNA (aVCN) | 0.97 | ND[b] | 0.21 | 0.03 | ND | 0.03 |
| Ratio by sc-ddPCR | 0.82 | 0.10 | 0.08 | 0.07 | ND | 0.01 |
| VCN/cell (tVCN) | 1.2 | ND | 2.61 | 0.4 | ND | 3.0 |

VCN, average VCN in the extracted genomic DNA;
ND, not detected;
tVCN, VCN in the fraction of transduced cells.
[a]The number of signals for vector ψ was slightly higher than that for RPP30. The actual ratio of vector ψ to RPP30 was 1.006 (100.6%).
[b]The aVCN measured in genomic DNA was lower than 0.005, and we could not calculate the tVCN, Representative data are shown.

Discussion

In hematopoietic SCGT, nonmyeloablative conditioning with busulfan has been performed to secure the BM niche for gene-transduced cells since a report by Aiuti et al (Non-Patent Literatures 6, 17, 19). By contrast, our patients did not receive preconditioning therapy, and they exhibited partial and temporal immune reconstitution (Non-Patent Literature 18). Inventors also reported that one of the patients later began to display gastrointestinal distress and failure to thrive, likely caused by incomplete immune recovery (Non-Patent Literature 20). Genetic and cytological analysis of the engraftment of gene-transduced cells was therefore imperative for evaluating the efficacy of treatment and assessing the influence of the protocol on their engraftment, but this was extremely difficult using conventional approaches.

Determining transduction efficiency at the genomic level has commonly been performed by PCR using genomic DNA samples after whole-genome amplification from a single cell (Non-Patent Literature 13) or colony-PCR using DNA from colony-forming cells (Non-Patent Literatures 21, 22). Although qPCR is effective for analyzing patients' genetic characteristics after gene therapy, there are some technical difficulties associated with a single-cell assay. A novel technology, ddPCR, was recently developed to enable the absolute quantification of nucleic acid target sequences. PCR with a TaqMan probe is performed within each droplet containing fragmented DNA, and the presence of the target gene is determined by counting the number of fluorescent signal-positive droplets (Non-Patent Literatures 23-25).

Based on this strategy, inventors established a new method for the absolute quantification of cells expressing the target gene. This novel system enables the direct detection of a target gene in a single cell without the extraction and amplification of genomic DNA. In establishing the strategy, inventors had some difficulties to overcome because the entire process from cell lysis to PCR amplification should be conducted within droplets. Inhibitors released from human blood cells such as lactoferrin (Non-Patent Literature 26) can inhibit direct PCR, and the target gene had to be amplified in the presence of these undesirable substances from lysed cells. Encapsulation of a single cell is another key factor for an accurate evaluation, because multi-cell encapsulation may lead to underestimation of the values. Increasing the PCR polymerase concentration and applying a low number of cells (2,000 cells) can provide precise amplification of the signal and make detailed analysis possible, even in small-scale cell samples.

The sc-ddPCR method enabled the detailed mapping of gene-transduced cells and revealed their complicated distribution in the specific cell fractions of patients' PB and BM samples. The results in both patients demonstrated the selective potential of ADA-positive cells over non-transduced cells in the T cell population. Pt2 received T cell-mediated gene therapy with the g-retrovirus vector LASN prior to SCGT (Non-Patent Literature 27), which could potentially explain the slightly lower levels of vector integration in T cells, as our primers and probe could not detect the LASN sequence. Meanwhile, lower ratios of vector-positive cells were detected in other cell fractions from PB and BM.

Remarkably, a small number of gene-transduced cells remained in the BM CD34+ cell population, which suggests that the circulating vector-positive cells in our patients are derived from the small population of "stem cells" in BM or from the differentiated precursors downstream of the HSCs. This also indicated that even in gene therapy for SCID, securing "space" in the BM niche was necessary for engineered HSCs to engraft and differentiate into multiple lineages.

Calculating the tVCN is also important in assessing the risk of insertional oncogenesis due to vector integration (Non-Patent Literatures 28-30), because it has been proposed that vector integration at a few copies per cell may reduce the number of potential hits (Non-Patent Literature 31). Using the sc-ddPCR system, inventors calculated the tVCNs in the treated patients and revealed that the transduced cells exhibited different levels of vector integration according to the lymphocyte lineage. In the experiments using K562 cells with various copy numbers (one to five copies) for evaluating this system, although spiked samples with one-copy cells had a coefficient of variation (CV) of more than 0.1, the calculated values ranged from 0.7 to 1.4, which could be determined as "1," and inventors concluded that the calculated values reflected the actual copy number.

Recently, ddPCR enabled the assessment of gene expression profiles within a single cell by performing the RT reaction inside droplets (Non-Patent Literature 32). In combination with RT, sc-ddPCR has the potential to detect transcription-active cells in the target population, and the difference in ratios between the vector-positive and transcription-active cells theoretically denotes "transcriptional suppression" in gene-transduced cells.

Overall, our novel system clarified vector integration in a single cell without any complex procedures, such as genome extraction and amplification, and single cell-based gene tracing allowed us to comprehensively analyze the engraftment of vector-transduced cells at the genetic level. Detailed information regarding the distribution of transduced cells in gene therapy-treated patients can be strongly advantageous for determining treatment strategies including conditioning therapy in SCGT clinical trials.

Materials and Methods

Generation of K562 Cells Carrying the GCsapM-ADA-Internal Ribosome Entry Site EGFP Retroviral Vector The original Molony murine leukemia virus (MoMLV)-based γ-retroviral vector GCsapM-ADA was described previously (Non-Patent Literature 33). A fragment of the internal ribosome entry site (IRES) and EGFP cDNA was incorporated downstream of ADA cDNA (GCsapM-ADA-IE). Virus supernatant was prepared by transfecting the 293 gpg packaging cell line (Non-Patent Literature 34) with the resultant vector plasmid using the calcium phosphate transfection method and was used to transduce K562 cells. After cloning by limiting dilution, genomic DNA was extracted from each clone, and VCNs were determined using the QX200 ddPCR system (Bio-Rad Laboratories) with primers and probes for vector packaging signals (Ψ) and the internal reference gene RPP30.

Patients

The patients' characteristics and detailed information about the clinical trial were previously described (Non-Patent Literature 18). In brief, Pt1 and Pt2 developed clinical symptoms at 15 days and 8 months after birth, respectively, and they were treated with SCGT at the ages of 4.7 and 13.0 years, respectively. PEG-ADA treatment was withdrawn, and no cytoreductive therapy was administered before SCGT in either patient.

Separation of Cell Subsets from PB and BM

Mononuclear cells were separated from the PB samples of both patients via density gradient centrifugation using Ficoll-Hypaque. Nuclear cells were collected from BM samples via erythrocyte lysis. Each immune phenotype subset was isolated by FACS using fluorescent-labeled antibodies (FACSAria II; BD Biosciences). The following monoclonal antibodies were used for positive selection: anti-CD3 (T cells), anti-CD19 (B cells), and anti-CD56 (NK cells).

Design of Primers and Probes for Fluorescent PCR

The following primers and probes were used for detecting the retrovirus packaging signal:

```
retrovirus Ψ forward,
5'-gcaacctatctgtgtctgtccg-3';

retrovirus Ψ reverse,
5'-ggtccgccagatacagag c-3';

retrovirus Ψ probe,
5'-/FAM/tgcgcctgc/ZEN/gtctgtactagttag/3IABkFQ/-3';

RPP30 forward,
5'-tccaggagggagaattga tg-3';

RPP30 reverse,
5'-atggtccgtctcaggaaa tg-3';
and

RPP30 probe,
5'-/HEX/tccctagg/ZEN/tggcctgagcag/3IABkFQ/-3'.
``` sc-ddPCR

The PCR reaction mixture consisted of a 20-mL solution containing 7.50 mL ddPCR supermix, the probe at a concentration of 0.5 or 1.0 mM, and 0.5 mM primers for the target Ψ and RPP30. 4 mL KAPA2G Hot Start DNA polymerase (KAPA Biosystems), 2.80 mL KAPA2G Hot Start buffer and enhancer, and SDS (0.015% final) were additionally applied to the mix, as described in Table 3. Sample cells were directly added, and droplets were generated using the Bio-Rad QX200 system following the manufacturer's instructions. The reactions were transferred to a 96-well plate for the PCR protocol using a C1000 Thermal Cycler (Bio-Rad). The thermal cycling program included the cell lysis step at 85° C. for 60 min, initial denaturation at 95° C. for 3 min, and 42 cycles of melting at 94° C. for 30 s, annealing at 60° C. for 60 s, and elongation at 72° C. for 60 s. After the additional extension at 72° C. for 10 min was completed, the 96-well plate was transferred to a QX200 Droplet Reader (Bio-Rad) and analyzed for the number of fluorescent-positive droplets. Detailed information about the composition of the reaction and PCR program is described in the Supplemental Information.

The ratio of vector-positive cells was calculated as follows:

$$\text{Ratio of vector-positive cells} = (\text{number of vector positive droplets})/(\text{number of RPP30-positive droplets}).$$

Genomic DNA Extraction and Conventional ddPCR

Genomic DNA was extracted from sorted cell subsets using a DNeasy Blood and Tissue Kit (QIAGEN) and then analyzed for vector Ψ and RPP30 copy numbers using multiplex ddPCR with standard procedures. For K562 cell samples spiked with one-copy K562-AE cells, the vector index was calculated as follows:

$$\text{Vector index} = (2 \times \text{number of vector-positive droplets})/(\text{number of RPP30-positive droplets}).$$

An index of 1 indicated that all cells contained the provirus sequence, meaning that each cell had two copies of RPP30 and one copy of vector Ψ. The aVCN was calculated using genomic DNA extracted from patients' samples as follows:

$$a\text{VCN}(\text{VCNs/cell}) = (\text{number of vector-positive droplets})/(0.5 \times \text{number of RPP30-positive droplets}).$$

Calculation of VCNs in Vector-Transduced Cells tVCNs were determined on the basis of the ratios of gene-transduced cells and aVCNs, calculated using sc-ddPCR and a conventional ddPCR, respectively. The tVCN in each cell was calculated as follows:

$$t\text{VCN} = a\text{VCN}/(\text{ratio of vector-positive droplets}).$$

Study Approval

All study protocols involving the participation of patients were approved by the ethics committees at the National Center for Child Health and Development (NCCHD). PB and BM samples were obtained from both patients after written informed consent was obtained from the patients' parents, in line with standard ethical procedures.

Supplemental Information

FIG. 6. Single-cell encapsulation of PBMCs and CB mononuclear cells. Pictures of encapsulated cells in droplets are shown. Encapsulation is not influenced by cell type. PBMC, peripheral blood mononuclear cell; CB, cord blood.

Figure 7:
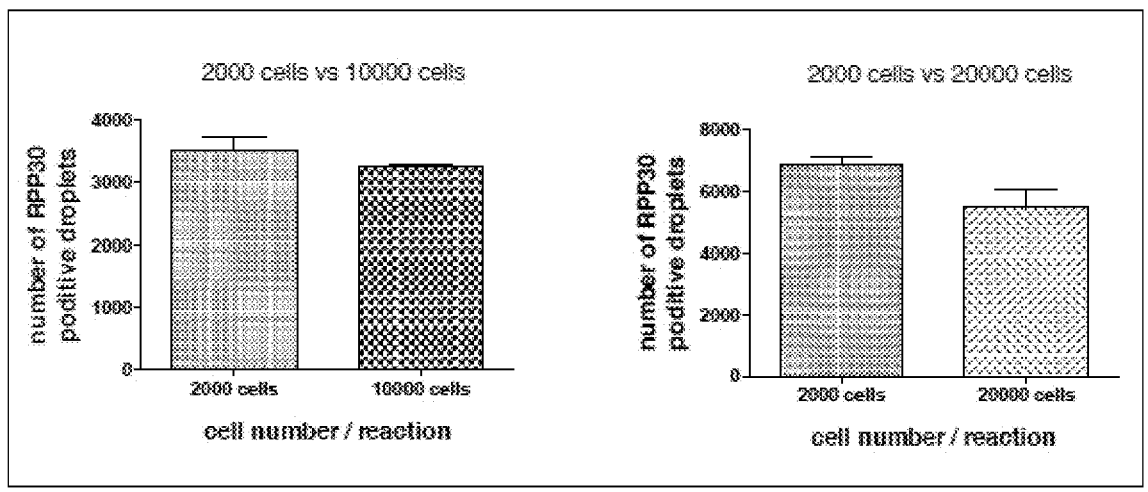
FIG. 7 shows Influence of multi-cell encapsulation on the absolute numbers of signal-positive droplets.

FIG. 7. Influence of multi-cell encapsulation on the absolute numbers of signal-positive droplets. Samples containing 10,000 or 20,000 cells were analyzed for RPP30 using two different encapsulation strategies as follows: a total of 5 or 10 reactions of 2000-cell samples; or the inclusion of all cells in one reaction (2,000 vs. 10,000, p=0.1492; 2,000 vs. 20,000, p=0.0175).

FIG. 8. Purity of FACS-sorted fractions of patient cells. Peripheral blood mononuclear cells obtained from the patients were sorted by FACS into CD3+, CD19+, and CD56+ populations for sc-ddPCR. Isolated CD19+ and CD56+ cell samples did not exhibit contamination by CD3+ cells.

TABLE 3

| Composition of the mixture used for dsPCR | |
|---|---|
| 2 × ddPCR mix for probe (186-3010) | 7.50 µl |
| 100-µM probe (for Target gene) | 0.19 µl |
| 100-µM primer-F (for Target gene) | 0.11 µl |
| 100-µM primer-R (for Target gene) | 0.11 µl |
| 100-µM probe (for Reference gene) | 0.095 µl |

TABLE 3-continued

Composition of the mixture used for dsPCR

| | |
|---|---|
| 100-µM primer-F (for Reference gene) | 0.11 µl |
| 100-µM primer-R (for Reference gene) | 0.11 µl |
| SDS | 0.015% |
| Hot start DNA polymerase (5 U/µl) | 4.00 U |
| 5 × KAPA2G Hot start buffer | 2.80 µl |
| 5 × KAPA2G Hot start enhancer | 2.80 µl |
| Cell sample (5 × $10^5$/ml) | 4.00 µl |
| Total volume | 20.1 µl |

TABLE 4

PCR program for sc-ddPCR

| Cycling step | Temperature, ° C. | Time | Ramp rate | Number of cycles |
|---|---|---|---|---|
| Cell lysis | 85 | 60 min | | 1 |
| Enzyme activation | 95 | 3 min | | 1 |
| Denaturation | 94 | 30 s | Approximately 2.0° C./s | |
| Annealing | 60 | 30 s | | 42 |
| Extension | 72 | 60 s | | |
| Additional extension | 72 | 2 min | | 1 |
| Cooling hold | 4-12 | ∞ | | |

*Use a heated lid set to 105° C. and set the sample volume to 40 µl.

TABLE 5

Clinical data at analysis

| | Number of lymphocytes | | |
|---|---|---|---|
| | Exam 1 (/µl) | Exam 2 (/µl) | Exam 3 (/µl) |
| Patient 1 | 228 | 435 | 199.8 |
| Patient 2 | 893 | 530 | 901 |

| | Number of nuclear cells in bone marrow Exam 1 (/µl) |
|---|---|
| Patient 1 | 43,300 |
| Patient 2 | 48,000 |

TABLE 6

Calculation of the copy number per cell in spiked cell samples

| | % of spiked K562-AE cells | | | | |
|---|---|---|---|---|---|
| | 100% | 50% | 25% | 10% | 5% |
| 5-copy sample (n = 3 for each dilution) | | | | | |
| VCN/cell (tVCN) | 5.40 | 4.75 | 4.16 | 4.46 | 4.63 |
| CV | 0.036 | 0.105 | 0.032 | 0.161 | 0.249 |
| 4-copy sample (n = 3 for each dilution) | | | | | |
| VCN/cell (tVCN) | 4.63 | 4.48 | 3.66 | 3.63 | 3.6 |
| CV | 0.110 | 0.028 | 0.043 | 0.084 | 0.120 |
| 2-copy sample (n = 3 for each dilution) | | | | | |
| VCN/cell (tVCN) | 2.23 | 2.24 | 2.19 | 2.20 | 2.11 |
| CV | 0.053 | 0.034 | 0.072 | 0.142 | 0.344 |
| 1-copy sample (n = 3 for each dilution) | | | | | |
| VCN/cell (tVCN) | 1.052 | 1.213 | 1.084 | 1.096 | 1.065 |
| CV | 0.176 | 0.142 | 0.177 | 0.279 | 0.031 |

Table 6. Calculation of the Copy Number Per Cell in Spiked Cell Samples.

Based on the average vector copy number (VCN) and the ratio of spiked cells, VCNs in spiked cell clones were calculated. The calculated values were extremely close to the actual values in all clones.

tVCN: VCN in the fraction of transduced cells; CV: coefficient of variation. The tVCN was determined on the basis of the ratios of vector-positive cells by sc-ddPCR and the average copy number (aVCN) via ddPCR using genomic DNA for each sample. The tVCN in each cell was calculated as follows: tVCN=aVCN/ratio of vector-positive cells.

ADDITIONAL EXAMPLES

The following description will discuss, as Additional Examples, the results of working and studying the present invention under conditions differing from those disclosed in the following literature: Yuka Igarashi, Toru Uchiyama, Tomoko Minegishi, Sirirat Takahashi, Nobuyuki Watanabe, Toshinao Kawai, Masafumi Yamada, Tadashi Ariga, and Masafumi Onodera. (2017). Molecular Therapy: Methods & Clinical Development Vol. 6, pp 6-16. (Hereinafter, this literature will be referred to as "literature of the present invention". This literature corresponds to [Example 1] described herein.

Additional Example 1: Study of Concentration of Surfactant

The droplet, which was prepared by the method disclosed in the "literature of the present invention" and which contained a cell that was not yet lysed, had a volume of approximately 20.1 µl and contained SDS. The final concentration of the SDS was approximately 0.015% (w/v) (the droplet was prepared with use of an SDS solution (0.2% (w/v)) so that the droplet contained the SDS solution in an amount of 1.5 µl).

In Additional Example 1, the droplets were prepared so as to each have a volume of approximately 20.1 µl and contain SDS whose final concentration was at least one of approximately 0.01% (w/v), approximately 0.015% (w/v), approximately 0.02% (w/v), approximately 0.025% (w/v), and approximately 0.05% (w/v) (that is, the following droplets were prepared: droplets containing an SDS solution of 0.2% (w/v) in an amount of 1 µl, droplets containing the SDS solution in an amount of 1.5 µl, droplets containing the SDS solution in an amount of 2 µl, droplets containing the SDS solution in an amount of 2.5 µl, and droplets containing the SDS solution in an amount of 5 µl). Other than the points above, a series of operations from lysing of a cell in a droplet through carrying out analysis by use of droplet digital PCR were performed according to the method disclosed in the "literature of the present invention".

As a result, in any of the experiments, it was possible to lyse the cell without disrupting the droplet, and to make PCR reaction. Note, however, that in a case where the final concentration of the SDS contained in the droplet was approximately 0.015% (w/v), the results of the analysis showed the highest sensitivity and highest specificity. Based on the results, the method disclosed in the "literature of the present invention" was established.

Additional Example 2: Adjustment of the Number of Cells Contained in Droplet

According to the method disclosed in the "literature of the present invention", the droplets containing cells that were not yet lysed had a volume of approximately 20.1 µl, and, with an extremely high probability, contained only a single cell per droplet. The study of the droplets showed that in a case where a liquid before droplets are formed contains cells at a concentration of $1.5 \times 10^5$ cells/ml or less, it is possible to obtain, with an extremely high probability, a droplet containing only a single cell.

From the viewpoint of increasing the probability of a droplet containing only a single cell, it is enough that a liquid before droplets are formed contains cells at a concentration of $2 \times 10^5$ cells/ml or less (preferably at a concentration of $1.5 \times 10^5$ cells/ml or less) without any limits to a lower limit of the concentration. Note, however, that from the viewpoint of securing a sufficient number of signals for analysis by use of droplet digital PCR, a liquid before droplets are formed preferably contains cells at a concentration of $1.5 \times 10^4$ cells/ml or more (preferably at a concentration of $5 \times 10^4$ cells/ml or more).

Additional Example 3: Optimization of Conditions in Case where Heating is Performed so as to Lyse Cells With respect to the droplets which were prepared according to the method disclosed in the "literature of the present invention" and which contained cells that were not yet lysed, the conditions under which to perform heating so as to lyse cells were studied. Other than the fact that the heating conditions for lysing cells were set as described below, a series of operations from lysing of the cell in a droplet through carrying out analysis by use of droplet digital PCR were performed according to the method disclosed in the "literature of the present invention". Note that, in (Study 2), KAPA2G Hot start DNA polymerase was used in an amount identical to the amount disclosed in the "literature of the present invention". (See also Table S1 and the description concerning sc-ddPCR in page 14, lower right column of the "literature of the present invention". Table S1 of the "literature of the present invention" corresponds to Table 3 in [Example 1] herein. The description concerning sc-ddPCR in page 14 of the "literature of the present invention" corresponds to the description concerning sc-ddPCR in [Example 1] herein). In (Study 1), unlike the "literature of the present invention", 4 units of KAPA2G Robust Hot start DNA polymerase (Kapa biosystems) were not added. Specifically, in (Study 1), only hot-start DNA polymerase contained in 2×ddPCR mix was used as polymerase for PCR.

(Study 1)
(1-1)
In a case where, for lysing the cells, the temperature for the heating was ranged from 30° C. to 54° C. and the heating time was constantly set to 15 minutes, no signal indicating PCR amplification was obtained. In any case where, for lysing the cells, the temperature for the heating was set to 95° C. and the heating time was set to 5 minutes, 10 minutes, 15 minutes, or 20 minutes, signals indicating PCR amplification were obtained in small amounts.

(1-2)
In any case where, for lysing the cells, the temperature for the heating was ranged from 70° C. to 90° C. and the heating time was constantly set to 1 hour, signals indicating PCR amplification were obtained. Substantially no non-specific PCR amplification was observed. It was determined that in these ranges of the temperatures, 88.8° C. was the best temperature condition (due to automatic gradient).

(1-3)
In a case where, for lysing the cells, the temperature for the heating was set to 88.5° C. and the heating time was set to 2 hours, signals indicating PCR amplification were obtained. Substantially no non-specific PCR amplification was observed. In terms of lysing of the cells, the results showed substantially no difference in comparison with the case where the heating time was set to 1 hour ((1-2) above).

(1-4)
In a case where the heating was divided into two stages so that a first heating stage was performed at 60° C. for 5 minutes and a second heating stage was performed at 37° C. or 47° C. for 8 hours, signals indicating PCR amplification were obtained. It was observed, however, that non-specific PCR amplification tended to occur.

The above study suggests that in a case where heating is performed so as to lyse cells, conditions of a relatively high temperature and a relatively short period of time (such as 0.5 hours to 1.5 hours or 0.7 hours to 1.3 hours) are particularly preferable.

(Study 2)
In any case where, for lysing the cells, the temperature for the heating was ranged from 66° C. to 90° C. and the heating time was set to 10 minutes or 1 hour, signals indicating PCR amplification were obtained in further sufficient amounts than in the case of (1-2) above. It was determined that among these conditions, conditions of 85° C. for 1 hour were the best conditions. The method disclosed in the "literature of the present invention" was thus established.

The results of (Study 1) and (Study 2) show that although the amount of DNA polymerase for use in PCR amplification can be identical to the amount in the cases of ordinary droplet digital PCR, it is preferable to separately add heat-resistant PCR polymerase (for example, in an amount which is, in comparison with an ordinary amount (0.1 units/20 μl), 5 times or more, 10 times or more, 20 times or more, 30 times or more, 40 times or more, or 45 times as much).

The present invention is not limited to the description of the embodiments and examples above, but may be altered by a skilled person within the scope of the claims. An embodiment based on a proper combination of technical means disclosed in different embodiments is encompassed in the technical scope of the present invention.

INDUSTRIAL APPLICABILITY

The present invention provides new method of amplifying a polynucleotide of interest.

[Sequence Listing]

Sequence Listing

The invention claimed is:

1. A method of amplifying a target nucleic acid contained in a cell, comprising the steps of:
   lysing the cell which is stored in a droplet constituted by a liquid in an amount of 100 ml or less, by a combination of heating and use of a surfactant with a predetermined concentration of 0.005% (w/v)-0.1% (w/v), the surfactant being contained in the droplet; and
   amplifying the target nucleic acid in the droplet;
   wherein a result of the amplifying of the target nucleic acid in each droplet is visualized; and
   the result is read by a reader.

2. The method according to claim 1, wherein the cell is a stem cell or a cell derived from the stem cell.

3. The method according to claim 1, wherein the cell is a cell collected from a living body.

4. The method according to claim 1, wherein the cell contains, as the target nucleic acid, (i) a nucleic acid for gene therapy or (ii) a genetically recombinant nucleic acid.

5. The method according to claim 1, wherein the surfactant is an anionic surfactant.

6. The method according to claim 1, wherein:
   the heating is carried out to raise a temperature to 40° C. or higher.

7. The method according to claim 6, wherein the heating is carried out immediately before the amplifying of the target nucleic acid or carried out as a step involved in an operation for the amplifying of the target nucleic acid.

8. The method according to claim 1, wherein a desired number of cells are stored in each of 70% or more of the droplets.

9. The method according to claim 1, wherein the droplet in which a desired number of cells are stored is formed from the liquid containing a plurality of the cells.

10. The method according to claim 1, wherein the amplifying of the target nucleic acid is carried out by PCR.

11. The method according to claim 1, wherein the liquid contains a composition for amplifying the target nucleic acid.

12. The method according to claim 1, wherein
   the target nucleic acid to be amplified is
   1) a nucleic acid for gene therapy or a genetically recombinant nucleic acid
   2) a DNA in a genome contained in the cell or is a DNA in a cytoplasm contained in the cell, or
   3) a marker nucleic acid characterizing the cell containing the target nucleic acid.

13. The method according to claim 12, wherein the marker nucleic acid characterizes an abnormal cell.

14. The method according to claim 1, further comprising the step of:
   detecting, on the basis of a result of amplifying of a target nucleic acid(s), 1) a ratio of a cell(s) containing the target nucleic acid(s) or 2) presence/absence of a cell(s) containing the target nucleic acid(s).

15. The method according to claim 1, further comprising the step of:
   (i) evaluating, on the basis of a result of amplifying of the target nucleic acid, a quality of the cell or (ii) identifying, on the basis of a result of the amplifying of the target nucleic acid, a type of the cell.

16. The method according to claim 5, wherein the anionic surfactant is SDS.

17. The method according to claim 1, wherein the concentration of the surfactant is 0.01% (w/v)-0.05% (w/v).

18. The method according to claim 5, wherein the concentration of the surfactant is 0.01% (w/v)-0.05% (w/v).

* * * * *